United States Patent
Morgan et al.

(10) Patent No.: US 6,265,213 B1
(45) Date of Patent: Jul. 24, 2001

(54) COMPOSITIONS AND METHODS FOR DETERMINING THE ACTIVITY OF DNA-BINDING PROTEINS AND OF INITIATION OF TRANSCRIPTION

(75) Inventors: Antony R. Morgan, deceased, late of Edmonton; by Robert Charles Morgan, executor, Toronto; Alberto Severini, Edmonton, all of (CA)

(73) Assignee: DNAB Diagnostics, Inc., Edmonton (CA)

( * ) Notice: Subject to any disclaimer, the term of this patent is extended or adjusted under 35 U.S.C. 154(b) by 0 days.

(21) Appl. No.: 09/593,323

(22) Filed: Jun. 13, 2000

Related U.S. Application Data

(62) Division of application No. 09/344,300, filed on Jun. 24, 1999.

(51) Int. Cl.[7] .............................. C12N 15/00; C12N 9/16; C12Q 1/68; C07K 1/00; C07H 21/04
(52) U.S. Cl. .................... 435/320.1; 435/196; 435/6; 530/350; 536/23.1
(58) Field of Search .............................. 435/320.1, 478.8, 435/196, 199, 6; 530/350; 536/23.1

(56) References Cited

FOREIGN PATENT DOCUMENTS

WO 9210578   of 1992  (WO).

OTHER PUBLICATIONS

Sodeoka et al. A Multifunctional Plasmid for Protein Expression by ECPCR: Overproduction of the p50 Subunit of NF–kB. Bioorganic and Medicinal Chemistry letters, vol. 3, No. 6, pp. 1089–1094, Jun. 1993.*

Lakin (1993) In: "Transcription Factors. A Practical Approach" Latchman, D.S. editor, pp. 27–47. IRL Press, New York.

Dent and Latchman (1993) The DNA mobility shift assay in *Transcription Factors. A Practical Approach*, Latchman, D.S. editor, pp. 1–26. IRL Press, New York.

Morgan et al. (1979) "Review: Ethidium fluorescence assays, Part I. Physiochemical studies," Nucl. Acid Res. 7:547–569.

Morgan et al. (1979) "Review: Ethidium fluorescence assay, Part II. Enzymatic studies and DNA–protein interactions," Nucl. Acids Res. 7:571–594.

Dignam et al. (1983) "Accurate transcription initiation by RNA polymerase II in a soluble extract from isolated mammalian nuclei," Nucl. Acid Res. 11:1475–1489.

Muller et al. (1995) "Structure of the NF–kB p50 homodimer bound to DNA," Nature 373:311–317.

Amman et al. (1983) "Vectors bearing a hybrid *tri–lac* promoter useful for regulated expression of cloned genes in *Escherichia coli*," Gene 25:167–178.

Johnson et al. (1980) "Bacteriophage λ Repressor and cro Protein: Interactions with Operator DNA," Methods Enzymol. 65:839–856.

Severini and Morgan (1991) "An Assay for Proteinases and Their Inhibitors Based on DNA/Ethidium Bromide Fluorescence," Anal. Biochem. 193:83–89.

Sodeoka et al. (1993) "A Multifunctional Plasmid for Protein Expression B Overproduction of the p50 Subunit of NF–kB," Bioorganic & Medicinal Chemistry Letters 3:1089–1094.

\* cited by examiner

*Primary Examiner*—Stephanie W. Zitomer
*Assistant Examiner*—Cynthia Wilder
(74) *Attorney, Agent, or Firm*—Medlen & Carroll, LLP

(57) ABSTRACT

This invention provides plasmids that are useful in detecting and determining the DNA-binding activity of sequence-specific DNA-binding molecules. The invention further provides plasmids that are useful in detecting and determining the activity of RNA polymerases in initiating transcription. In particular, the invention relates to plasmids that contain unique restriction sites and cognate nucleotide recognition sequences for sequence-specific DNA-binding molecules. Also provided are methods for using the plasmids disclosed herein.

8 Claims, 11 Drawing Sheets

NF-kB

TATA BINDING PROTEIN

LAMBDA REPRESSOR

RNA POLYMERASE

COMPOSITIONS AND METHODS FOR DETERMINING THE ACTIVITY OF DNA-BINDING PROTEINS AND OF INITIATION OF TRANSCRIPTION

This is a Divisional of co-pending application Ser. No. 09/344,300 filed on Jun. 24, 1999.

FIELD OF THE INVENTION

This invention relates to plasmids that are useful in detecting and determining the DNA-binding activity of sequence-specific DNA-binding molecules. The invention further relates to plasmids that are useful in detecting and determining the activity of RNA polymerases in initiating transcription. In particular, the invention relates to plasmids that contain unique restriction sites and cognate nucleotide recognition sequences for sequence-specific DNA-binding molecules. The invention further relates to methods for using the compositions disclosed herein.

BACKGROUND OF THE INVENTION

A. Sequence-Specific DNA-Binding Molecules And Diseases

Because of their involvement in disease development and progression, determining the presence and activity of sequence-specific DNA-binding molecules is of great importance in the diagnosis, and treatment of disease. For example, sequence-specific DNA-binding molecules that are involved in the development and progression of cancer are potential targets for anti-cancer drugs. In particular, the estrogen-receptor is a sequence-specific DNA-binding protein that is required for the growth of certain breast tumors. Detection of the sequence-specific DNA binding activity of the estrogen receptor in breast tumor cells allows rational selection of therapeutic drugs (e.g., tamoxifen) that bind to the estrogen-receptor and inhibit its ability to bind to DNA. Additionally, the availability of assays for the sequence-specific DNA binding activity of the estrogen-receptor is valuable in the discovery, screening and development of anti-estrogen drugs.

Similarly, assays for other sequences-specific DNA-binding molecules (e.g., hormone receptors) are also valuable for screening the sequence-specific DNA binding activity of anti-testosterone drugs for the treatment of prostate cancer. Assays for the sequence-specific DNA binding hormone receptor for cortisone are also useful since cortisone is an anti-inflammatory agent that potentiates anti-cancer chemotherapy by reducing the levels of NFκB and of other sequence-specific DNA-binding molecules that, among other actions, protect cancer cells from programmed cell death (apoptosis). Assays of sequence-specific DNA binding activity of molecules (e.g., RNA polymerases, TATA box binding protein) that are targeted by antiviral and antibacterial drugs are also useful in developing and screening candidate drugs.

B. Current Assays

Currently available methods for measuring the presence of sequence-specific DNA-binding molecules include immunological assays, DNA-binding assays, and expression assays. In immunological assays (e.g. fluorescence microscopy, ELISA, Western blotting), an antibody or antiserum is produced using the purified sequence-specific DNA-binding molecule. The antibodies are then used to detect the presence of the sequence-specific DNA-binding molecule in test samples. While these methods are specific and sensitive, they require several hours or days to complete. Importantly, immunological methods suffer from the drawback that they determine only the presence, not the sequence-specific DNA binding activity, of a sequence-specific DNA-binding molecule.

DNA-binding assays include gel retardation assays and DNA footprinting. In gel retardation assays, a double stranded synthetic oligonucleotide is constructed, having the specific nucleotide sequence to that the sequence-specific DNA-binding protein binds. The oligonucleotide is labeled, usually with radioactive phosphate, and incubated with the preparation containing the DNA-binding protein. The oligonucleotide is then electrophoresed on a suitable gel. The binding of a sequence-specific DNA-binding protein is detected as a retardation in the migration of the radioactive oligonucleotide. In DNA "foot printing" assays, a radioactively-labeled DNA molecule containing the DNA sequence to that the sequence-specific DNA-binding molecule binds is incubated with the sequence-specific DNA-binding molecule and then digested with DNAaseI, an enzyme that cuts DNA molecules regardless of their sequence. This forms DNA fragments of all possible lengths that can be separated by sequencing gel electrophoresis. A "ladder" of these different length fragments is formed on the gel. Binding of the sequence-specific DNA-binding molecule to its cognate nucleotide recognition sequence protects the DNA in that region from digestion with DNAaseI. This protection is observed as a region of reduced intensity of radioactivity on a sequencing gel, ie., the "ladder" is missing contiguous "rungs" where the protein was bound.

While DNA-binding assays are specific and sensitive, they nonetheless are laborious, requiring 1 to 7 days to perform, and are technically difficult. In addition, the gel retardation assay is suitable only for use with proteins that bind the DNA with very high affinity, since this assay requires that the protein remains bound to the DNA under the condition of extreme dilution used during gel electrophoresis. More importantly, both gel retardation assays and DNA footprinting assays are not quantitative.

Expression assays are directed to measuring the activity of sequence-specific DNA-binding molecules that function as gene regulators. This activity is assessed by measuring the ability of the gene regulator to induce or suppress the production of a specific mRNA or protein. This is done by inserting the nucleotide sequence upstream of a "reporter" gene and introducing the resulting vector into cells or into a suitable cell free in vitro system. The addition of the gene regulator modifies expression of the reporter gene. Expression assays are technically complex, time consuming (require several days or weeks to perform), and are not quantitative.

Other methods are available that measure the presence and/or activity of particular sequence-specific DNA-binding molecules. For example, the activity of the estrogen receptor in binding estrogen may be measured using radioactive estrogen. Similarly, RNA polymerase activity in initiating DNA transcription may be measured by quantitating the amount of RNA produced from a DNA template. Although these methods may be sensitive, specific, and quantitative for the particular molecule whose activity they are designed to measure, they are nevertheless not universally applicable to any sequence-specific DNA-binding molecule.

C. RNA Polymerases

RNA polymerases constitute a family of enzymes that transcribe DNA sequences into complementary RNA molecules. Because of the universality of the role of RNA polymerases in transcription in all cell types, the availability of assays to measure transcription activity of RNA polymerases is a valuable tool both in basic and applied research, and in the screening of inhibitors of RNA polymerases as antibacterial, antiviral, and anti-cancer drugs.

Currently available assays for RNA polymerase transcription activity measure production of RNA molecules. Transcription of specific genes is assayed in vitro by measuring the incorporation of radioactive uridine into transcribed RNA molecules that are produced from a defined DNA template in the presence of cell extracts containing RNA polymerase and all the required transcription factors. Transcription of specific genes can also be performed in cell cultures by detecting the production of specific mRNAs (e.g., by Northern blots) or by detecting the production of specific proteins (e.g., by immunoassays). Currently available assays for RNA polymerase transcription activity suffer from the disadvantages that they are laborious, complex, and require the use of radioactive isotopes.

Thus what is needed are compositions and methods for detecting and determining the DNA-binding activity of sequence-specific DNA-binding molecules. Also needed, are compositions and methods for detecting and determining the activity of RNA polymerases in initiating transcription.

SUMMARY OF THE INVENTION

The present invention provides compositions and methods for detecting the presence, determining the amount and concentration of sequence-specific DNA-binding molecules, and determining the amount and concentration of compounds that affect the DNA binding activity of a sequence-specific DNA-binding molecule. The invention further provides compositions and methods for detecting the presence of RNA polymerases, for determining the activity of RNA polymerases in initiating transcription, and for determining the presence and activity of compounds that affect initiation of transcription by RNA polymerases.

In particular, the invention provides a recombinant plasmid comprising: (a) a first region comprising a nucleotide sequence capable of specifically binding to a sequence-specific DNA-binding molecule; (b) a second region comprising a nucleotide sequence capable of binding to a restriction enzyme; and (c) a restriction site for the restriction enzyme; wherein the restriction site is located at a position selected from being within the first nucleotide sequence, within the second nucleotide sequence, substantially adjacent to the first nucleotide sequence, and substantially adjacent to the second nucleotide sequence.

Without intending to limit the invention to any particular location of the restriction site or to any particular plasmid, in one embodiment, the restriction site is comprised within the first nucleotide sequence, and the plasmid is selected from pDNAB-NFκB, pDNAB-TATA and pDNABtac. In an alternative embodiment, the restriction site is comprised within the second nucleotide sequence, and the plasmid is pDNAB-or1. In another embodiment, the restriction site is substantially adjacent to the first nucleotide sequence, and the plasmid is pDNAB-or1. In yet another embodiment, the restriction site is substantially adjacent to the second nucleotide sequence, and the plasmid is selected from pDNAB-NFκB, pDNAB-TATA and pDNABtac.

While not intending to limit the invention to a particular restriction enzyme, in a further embodiment, the restriction enzyme is selected from AatII, AccI, AflII, AflIII, AhaII, AluI, AlwI, AlwNI, ApaI, ApaLI, AseI, Asp718, AvaI, AvaII, AvrII, BalI, BamHI, BanI, BanII, BbeI, BbvI, BbvII, BclI, BcnI, BglI, BglII, BseRIBsmI, BsmAI, Bsp1286I, BspHI, BspMI, BspII, BsrI, BssHII, BstBI, BstEII, BstNI, BstUI, BstXI, BstYI, Bsu36I, Cfr10I, ClaI, DdeI, DpnI, DraI, DraIII, EaeI, EagI, EarI, Eco47III, EcoNI, EcoO109I, EcoRI, EcoRII, EcoRV, EspI, Fnu4HI, FokI, FspI, GdiII, HaeI, HaeII, HaeIII, HgaI, HgiAI, HhaI, HinCII, HinDIII, HinfI, HinPI, HpaI, HpaII, HphI, KpnI, MaeI, MaeII, MaeIII, MboI, MboII, MluI, MnlI, MseI, MspI, NaeI, NarI, NciI, NcoI, NdeI, NheI, NlaIII, NlaIV, NotI, NruI, NsiI, Nsp7524I, NspBII, NspHI, PaeR7I, PflMI, PleI, PpuMI, PstI, PvuI, PvuII, RsaI, RsrII, SacI, SacII, SalI, Sau3AI, Sau96I, ScaI, ScrFI, SecI, SfaNI, SfiI, SmaI, SnaBI, SpeI, SphI, SplI, SspI, StuI, StyI, TaqI, Tth111I, Tth111II, XbaI, XcaI, XhoI, XmaI, XmnI.

Without intending to limit the invention to a particular sequence-specific DNA-binding molecule, in yet a further embodiment, the sequence-specific DNA-binding molecule is selected from nucleic acid sequence, amino acid sequence, derivative of nucleic acid sequence and derivative of amino acid sequence. In a preferred embodiment, the sequence-specific DNA-binding molecule is a protein selected from λ cI repressor, TATA box binding protein, NFκB, bacterial mercury repressor, bacterial lac repressor, progesterone repressor, estrogen receptor, glucocorticoid receptor, androgen receptor, retinoid receptor family, thyrorid receptor, p53, lac suppressor, AraC, DnaA, MerR, HSV-1 ICP4, UL9, c-Myc/c-Max, RecBCD, γ/δ resolvase, λ bacteriophage integrase complex, DNA photolyase, Ada protein, methylated Ada protein, Rag1/Rag2, bacterial RNA polymerase, c-Jun, AP2, SP1, TFIIB, vitamin D receptor, AP-1 complex, Sp1, CREB family, CIEBP family, Egr family, Ets family, Stat family, NF-1 family, YY1, Ap-2 factors, E2F family, IRF family, MEF-2, Myo-D/Myo-E, Oct family, Pit-1, USF-1/USF-2, c-Myb, Pbx-1, GATA family, NF-E2, serum response factor, T7 bacteriophage RNA polymerase, T3 bacteriophage RNA polymerase, SP6 bacteriophage RNA polymerase, eukaryotic RNA polymerase I, eukaryotic RNA polymerase II, eukaryotic RNA polymerase III, PBS1 phage RNA polymerase, PBS2 phage RNA polymerase, vaccinia virus RNA polymerase, *Escherichia coli* RNA polymerase, and mitochondrion RNA polymerase.

The invention further provides a method for detecting the presence of a sequence-specific DNA-binding molecule capable of specifically binding to a nucleotide sequence, comprising: (a) providing: (i) a first sample suspected of containing a sequence-specific DNA-binding molecule capable of specifically binding to a first nucleotide sequence; (ii) a restriction enzyme capable of binding to a second nucleotide sequence and cleaving at a restriction site; and (iii) a recombinant plasmid comprising the first and second nucleotide sequences and the restriction site, wherein the restriction site is located at a position selected from being within the first nucleotide sequence, within the second nucleotide sequence, substantially adjacent to the first nucleotide sequence, and substantially adjacent to the second nucleotide sequence; and (b) contacting the first sample with the recombinant plasmid to generate a contacted sample, under conditions such that the sequence-specific DNA-binding molecule specifically binds to the first nucleotide sequence in the recombinant plasmid to generate a bound plasmid; (c) treating the contacted sample with the restriction enzyme under conditions such that the bound plasmid is not substantially cleaved by the restriction enzyme; and (d) detecting the presence of uncleaved plasmid in the contacted sample, thereby detecting the presence of the sequence-specific DNA-binding molecule in the first sample. In one embodiment, the method further comprises (e) determining the amount of the sequence-specific DNA-binding molecule in the first sample. In another embodiment, the method further comprises (e) determining the concentration of the sequence-specific DNA-binding molecule in the first sample.

Without intending to limit the invention to the location of the restriction site or to the type of plasmid, in yet another embodiment, the restriction site is comprised within the first nucleotide sequence, and the plasmid is selected from pDNAB-NFκB, pDNAB-TATA and pDNABtac. In a further embodiment, the restriction site is comprised within the second nucleotide sequence, and the plasmid is pDNAB-or1. In yet another embodiment, the restriction site is substantially adjacent to the first nucleotide sequence, and the plasmid is pDNAB-or1. In an additional embodiment, the restriction site is substantially adjacent to the second nucleotide sequence, and the plasmid is selected from pDNAB-NFκB, pDNAB-TATA and pDNABtac. In yet another embodiment, the restriction enzyme is selected from AatII, AccI, AflII, AflIII, AhaII, AluI, AlwI, AlwNI, ApaI, ApaLI, AseI, Asp718, AvaI, AvaII, AvrII, BalI, BamHI, BanI, BanII, BbeI, BbvI, BbvII, BclI, BenI, BglI, BglII, BseRIBsmI, BsmAI, Bsp1286I, BspHI, BspMI, BspMII, BsrI, BssHI, BstBI, BstEII, BstNI, BstUI, BstXI, BstYI, Bsu36I, Cfr101, ClaI, DdeI, DpnI, DraI, DraIII, EaeI, EagI, EarI, Eco47III, EcoNI, EcoO109I, EcoRI, EcoRII, EcoRV, EspI, Fnu4HI, FokI, FspI, GdiII, HaeI, HaeII, HaeIII, HgaI, HgiAI, HhaI, HinCII, HinDIII, HinfI, HinPI, HpaI, HpaII, HphI, KpnI, MaeI, MaeII, MaeIII, MboI, MboII, MluI, MnlI, MseI, MspI, NaeI, NarI, NciI, NcoI, NdeI, NheI, NlaIII, NlaIV, NotI, NruI, NsiI, Nsp7524I, NspBII, NspHI, PaeR7I, PflMI, PleI, PpuMI, PstI, PvuI, PvuII, RsaI, RsrII, SacI, SacII, SalI, Sau3AI, Sau96I, ScaI, ScrFI, SecI, SfaNI, SfiI, SmaI, SnaBI, SpeI, SphI, SplI, SspI, StuI, StyI, TaqI, Tth111I, Tth111II, XbaI, XcaI, XhoI, XmaI, XmnI.

While not intending to limit the invention to any particular sequence-specific DNA-binding molecule, the sequence-specific DNA-binding molecule is selected from nucleic acid sequence, amino acid sequence, derivative of nucleic acid sequence and derivative of amino acid sequence. In a more preferred embodiment, the sequence-specific DNA-binding molecule is a protein selected from λ cI repressor, TATA box binding protein, NFκB, bacterial mercury repressor, bacterial lac repressor, progesterone repressor, estrogen receptor, glucocorticoid receptor, androgen receptor, retinoid receptor family, thyrorid receptor, p53, lac suppressor, AraC, DnaA, MerR, HSV-1 ICP4, UL9, c-Myc/c-Max, RecBCD, γ/δ resolvase, λ bacteriophage integrase complex, DNA photolyase, Ada protein, methylated Ada protein, Rag1/Rag2, bacterial RNA polymerase, c-Jun, AP2, SP1, TFIIB, vitamin D receptor, AP-1 complex, Sp1, CREB family, C/EBP family, Egr family, Ets family, Stat family, NF-1 family, YY1, Ap-2 factors, E2F family, IRF family, MEF-2, Myo-D/Myo-E, Oct family, Pit-1, USF-1USF-2, c-Myb, Pbx-1, GATA family, NF-E2, serum response factor, T7 bacteriophage RNA polymerase, T3 bacteriophage RNA polymerase, SP6 bacteriophage RNA polymerase, eukaryotic RNA polymerase I, eukaryotic RNA polymerase II, eukaryotic RNA polymerase III, PBS1 phage RNA polymerase, PBS2 phage RNA polymerase, vaccinia virus RNA polymerase, *Escherichia coli* RNA polymerase, and mitochondrion RNA polymerase.

Also provided by the invention is a method for determining DNA-binding activity of a sequence-specific DNA-binding molecule, comprising: (a) providing: (i) a test sample suspected of comprising a sequence-specific DNA-binding molecule capable of specifically binding to a first nucleotide sequence; (ii) a plurality of samples comprising known amounts of the sequence-specific DNA-binding molecule; (iii) a restriction enzyme capable of binding to a second nucleotide sequence and of cleaving a DNA sequence at a restriction site; and (iv) a recombinant plasmid comprising the first and second nucleotide sequences and the restriction site, wherein the restriction site is located at a position selected from being comprised within the first nucleotide sequence, being comprised within the second nucleotide sequence, being substantially adjacent to the first nucleotide sequence, and being substantially adjacent to the second nucleotide sequence; (b) contacting the test sample with the recombinant plasmid to generate a contacted test sample and contacting the plurality of samples with the recombinant plasmid to generate a contacted plurality of samples, wherein the contacting is under conditions such that the sequence-specific DNA-binding molecule specifically binds to the first nucleotide sequence in the recombinant plasmid to form a bound plasmid; (c) treating the contacted test sample with the restriction enzyme to generate a treated test sample and treating the contacted plurality of samples with the restriction enzyme to generate a treated plurality of samples, wherein the treatment is under conditions such that the bound plasmid is not substantially cleaved by the restriction enzyme; and (d) comparing the amount of uncleaved plasmid in the treated test sample with the amount of uncleaved plasmid in the treated plurality of samples, thereby determining DNA-binding activity of the sequence-specific DNA-binding molecule in the test sample. In one embodiment, instead of steps d) the method comprises d) comparing the amount of cleaved plasmid in the treated test sample with the amount of cleaved plasmid in the treated plurality of samples, thereby determining DNA-binding activity of the sequence-specific DNA-binding molecule in the test sample.

While not intending to limit the invention to a particular restriction site or plasmid, in another embodiment, the restriction site is comprised within the first nucleotide sequence, and the plasmid is selected from pDNAB-NFκB, pDNAB-TATA and pDNABtac. In yet another embodiment, the restriction site is comprised within the second nucleotide sequence, and the plasmid is pDNAB-or1. In an alternative embodiment, the restriction site is substantially adjacent to the first nucleotide sequence, and the plasmid is pDNAB-or1. In yet another alternative embodiment, the restriction site is substantially adjacent to the second nucleotide sequence, and the plasmid is selected from pDNAB-NFκB, pDNAB-TATA and pDNABtac.

Although it is not intended that the invention be limited to any particular restriction enzyme, in a further preferred embodiment, the restriction enzyme is selected from AatII, AccI, AflII, AflIII, AhaII, AluI, AlwI, AlwNI, ApaI, ApaLI, AseI, Asp718, AvaI, AvaII, AvrII, BalI, BamHI, BanI, BanII, BbeI, BbvI, BbvII, BclI, BcnI, BglI, BglII, BseRIBsmI, BsmAI, BspI286I, BspHI, BspMI, BspMII, BsrI, BssHI, BstBI, BstEII, BstNI, BstUI, BstXI, BstYI, Bsu36I, Cfr10I, ClaI, DdeI, DpnI, DraI, DraIII, EaeI, EagI, EarI, Eco47III, EcoNI, EcoO109I, EcoRI, EcoRII, EcoRV, EspI, Fnu4HI, FokI, FspI, GdiII, HaeI, HaeII, HaeIII, HgaI, HgiAI, HhaI, HinCII, HinDIII, HinfI, HinPI, HpaI, HpaII, HpII, KpnI, MaeI, MaeII, MaeIII, MboI, MboII, MluI, MnlI, MseI, MspI, NaeI, NarI, NciI, NcoI, NdeI, NheI, NlaIII, NlaIV, NotI, NruI, NsiI, Nsp7524I, NspBII, NspHI, PaeR7I, PflMI, PleI, PpuMI, PstI, PvuI, PvuII, RsaI, RsrII, SacI, SacII, SalI, Sau3AI, Sau96I, ScaI, ScrFI, SecI, SfaNI, SfiI, SmaI, SnaBI, SpeI, SphI, SplI, SspI, StuI, StyI, TaqI, Tth111I, Tth111I, XbaI, XcaI, XhoI, XmaI, XmnI.

While not intending to limit the invention to a particular sequence-specific DNA-binding molecule, in another embodiment, the sequence-specific DNA-binding molecule is selected from nucleic acid sequence, amino acid sequence, derivative of nucleic acid sequence and derivative of amino acid sequence. In a preferred embodiment, the sequence-specific DNA-binding molecule is a protein selected from λ cI repressor, TATA box binding protein, NFκB, bacterial mercury repressor, bacterial lac repressor, progesterone repressor, estrogen receptor, glucocorticoid receptor, androgen receptor, retinoid receptor family, thyrorid receptor, p53, lac suppressor, AraC, DnaA, MerR, HSV-1 ICP4, UL9, c-Myc/c-Max, RecBCD, γ/δ resolvase, λ bacteriophage integrase complex, DNA photolyase, Ada protein, methylated Ada protein, Rag1/Rag2, bacterial RNA polymerase, c-Jun, AP2, SP1, TFIIB, vitamin D receptor, AP-1 complex, Sp1, CREB family, C/EBP family, Egr family, Ets family, Stat family, NF-1 family, YY1, Ap-2 factors, E2F family, IRF family, MEF-2, Myo-D/Myo-E, Oct family, Pit-1, USF-1/ JUSF-2, c-Myb, Pbx-1, GATA family, NF-E2, serum response factor, T7 bacteriophage RNA polymerase, T3 bacteriophage RNA polymerase, SP6 bacteriophage RNA polymerase, eukaryotic RNA polymerase I, eukaryotic RNA polymerase II, eukaryotic RNA polymerase III, PBS1 phage RNA polymerase, PBS2 phage RNA polymerase, vaccinia virus RNA polymerase, *Escherichia coli* RNA polymerase, and mitochondrion RNA polymerase.

The invention additionally provides a method for detecting the presence of initiation of transcription activity by RNA polymerase, comprising: (a) providing: (i) a test sample suspected of comprising RNA polymerase capable of specifically binding to a first nucleotide sequence; (ii) a restriction enzyme capable of binding to a second nucleotide sequence and of cleaving a DNA sequence at a restriction site; (iii) a recombinant plasmid comprising the first and second nucleotide sequences and the restriction site, wherein the restriction site is located at a position selected from being comprised within the first nucleotide sequence, being comprised within the second nucleotide sequence, being substantially adjacent to the first nucleotide sequence, and being substantially adjacent to the second nucleotide sequence; and (iv) a mixture of ribonucleotide triphosphates; (b) contacting the test sample with the recombinant plasmid to generate a contacted test sample, wherein the contacting is under conditions such that the RNA polymerase specifically binds to the first nucleotide sequence in the recombinant plasmid to form a bound plasmid; (c) treating the contacted test sample with the restriction enzyme to generate a treated test sample, wherein the treatment is under conditions such that the bound plasmid is not substantially cleaved by the restriction enzyme; (d) mixing the treated test sample with the mixture of ribonucleotide triphosphates to generate a mixed test sample; and (e) detecting the presence of uncleaved plasmid in the mixed test sample thereby detecting the presence of the initiation of transcription activity by the RNA polymerase in the test sample.

In one embodiment, instead of steps e) the method comprises e) detecting the presence of cleaved plasmid in the mixed test sample thereby detecting the presence of the initiation of transcription activity by the RNA polymerase in the test sample. In another embodiment, the test sample further comprises an inhibitor of initiation of transcription activity.

While not intending to limit the invention to a particular restriction site or plasmid, in yet another embodiment, the restriction site is comprised within the first nucleotide sequence, and the plasmid is pDNABtac. In an alternative embodiment, the restriction site is substantially adjacent to the second nucleotide sequence, and the plasmid is pDNABtac.

It is not intended that the invention be limited to a particular restriction enzyme. However, in yet another alternative embodiment, the restriction enzyme is selected from AatII, AccI, AflII, AflIII, AhaII, AluI, AlwI, AlwNI, ApaI, ApaLI, AseI, Asp718, AvaI, AvaII, AvrII, BalI, BamHI, BanI, BanII, BbeI, BbvI, BbvII, BclI, BcnI, BglI, BglII, BseRIBsmI, BsmAI, Bsp1286I, BspHI, BspMI, BspMII, BsrI, BssHII, BstBI, BstEII, BstNI, BstUI, BstXI, BstYI, Bsu36I, Cfr10I, ClaI, DdeI, DpnI, DraI, DraIII, EaeI, EagI, EarI, Eco47III, EcoNI, EcoO109I, -EcoRI, EcoRII, EcoRV, EspI, Fnu4HI, FokI, FspI, GdiII, HaeI, HaeII, HaeIII, HgaI, HgiAI, HhaI, HinCII, HinDIII, HinfI, HinPI, HpaI, HpaII, HphI, KpnI, MaeI, MaeII, MaeIII, MboI, MboII, MuluI, MnlI, MseI, MspI, NaeI, NarI, NciI, NcoI, NdeI, NheI, NlaIII, NlaIV, NotI, NruI, NsiI, Nsp7524I, NspBII, NspHI, PaeR7I, PflMI, PleI, PpuMI, PstI, PvuI, PvuII, RsaI, RsrII, SacI, SacII, SalI, Sau3AI, Sau96I, ScaI, ScrFI, SecI, SfaNI, SfiI, SmaI, SnaBI, SpeI, SphI, SplI, SspI, StuI, StyI, TaqI, Tth111I, Tth111I, XbaI, XcaI, XhoI, XmaI, XmnI.

While not intending to limit the invention to any particular RNA polymerase, in a further embodiment, the RNA polymerase is selected from T7 bacteriophage RNA polymerase, T3 bacteriophage RNA polymerase, SP6 bacteriophage RNA polymerase, eukaryotic RNA polymerase I, eukaryotic RNA polymerase II, eukaryotic RNA polymerase III, PBS1 phage RNA polymerase, PBS2 phage RNA polymerase, vaccinia virus RNA polymerase, *Escherichia coli* RNA polymerase, and mitochondrion RNA polymerase.

Also provided herein is a method for determining initiation of transcription activity by RNA polymerase, comprising: (a) providing: (i) a test sample suspected of comprising RNA polymerase capable of specifically binding to a first nucleotide sequence; (ii) a plurality of samples comprising known amounts of the RNA polymerase; (iii) a restriction enzyme capable of binding to a second nucleotide sequence and of cleaving a DNA sequence at a restriction site; (iv) a recombinant plasmid comprising the first and second nucleotide sequences and the restriction site, wherein the restriction site is located at a position selected from being comprised within the first nucleotide sequence, being comprised within the second nucleotide sequence, being substantially adjacent to the first nucleotide sequence, and being substantially adjacent to the second nucleotide sequence; and (v) a mixture of ribonucleotide triphosphates; (b) contacting the test sample with the recombinant plasmid to generate a contacted test sample and contacting the plurality of samples with the recombinant plasmid to generate a contacted plurality of samples, wherein the contacting is under conditions such that the RNA polymerase specifically binds to the first nucleotide sequence in the recombinant plasmid to form a bound plasmid; (c) treating the contacted test sample with the restriction enzyme to generate a treated test sample and treating the contacted plurality of samples with the restriction enzyme to generate a treated plurality of samples, wherein the treatment is under conditions such that the bound plasmid is not substantially cleaved by the restriction enzyme; (d) mixing the treated test sample with the mixture of ribonucleotide triphosphates to generate a mixed test sample and mixing the treated plurality of samples with the mixture of ribonucleotide triphosphates to generate a mixed plurality of samples; and (e) comparing the amount of uncleaved plasmid in the mixed test sample with the amount of uncleaved plasmid in the mixed plurality of samples, thereby determining initiation of transcription activity of the RNA polymerase in the test sample.

In one embodiment, instead of steps e) the method comprises e) comparing the amount of cleaved plasmid in the treated test sample with the amount of cleaved plasmid in the treated plurality of samples, thereby determining transcription activity of the RNA polymerase in the test sample. In another embodiment, the test sample further comprises an inhibitor of initiation of transcription activity.

Without intending to limit the invention to any particular restriction site or plasmids, in yet another embodiment, the restriction site is comprised within the first nucleotide sequence, and the plasmid is pDNABtac. In an alternative embodiment, the restriction site is substantially adjacent to the second nucleotide sequence, and the plasmid is pDNABtac.

Although it is not intended that the invention be limited to a particular restriction enzyme, in yet another alternative embodiment, the restriction enzyme is selected from AatII, AccI, AflI, AflIII, AhaII, AluI, AlwI, AlwNI, ApaI, ApaLI, AseI, Asp718, AvaI, AvaII, AvrII, BalI, BamHI, BanI, BanII, BbeI, BbvI, BbvII, BclI, BcnI, BglI, BglII, BseRIBsmI, BsmAI, Bsp1286I, BspHI, BspMI, BspMII, BsrI, BssHII, BstBI, BstEII, BstNI, BstUI, BstXI, BstYI, Bsu36I, Cfr10I, ClaI, DdeI, DpnI, DraI, DraIII, EaeI, EagI, EarI, Eco47III, EcoNI, EcoO109I, EcoRI, EcoRII, EcoRV, EspI, Fnu4HI, FokI, FspI, GdiII, HaeI, HaeII, HaeIII, HgaI, HgiAI, HhaI, HinCII, HinDIII, HinfI, HinPI, HpaI, HpaII, HphI, KpnI, MaeI, MaeII, MaeIII, MboI, MboII, MuI, MnlI, MseI, MspI, NaeI, NarI, NciI, NcoI, NdeI, NheI, NlaIII, NlaIV, NotI, NruI, NsiI, Nsp7524I, NspBII, NspHI, PaeR7I, PflMI, PleI, PpuMI, PstI, PvuI, PvuII, RsaI, RsrII, SacI, SacII, SalI, Sau3AI, Sau96I, ScaI, ScrFI, SecI, SfaNI, SfiI, SmaI, SnaBI, SpeI, SplI, SplII, SspI, StuI, StyI, TaqI, Tth111I, Tth111II, XbaI, XcaI, XhoI, XmaI, XmnI.

While not intending to limit the invention to any particular RNA polymerase, in a further embodiment, the RNA polymerase is selected from T7 bacteriophage RNA polymerase, T3 bacteriophage RNA polymerase, SP6 bacteriophage RNA polymerase, eukaryotic RNA polymerase I, eukaryotic RNA polymerase II, eukaryotic RNA polymerase III, PBSI phage RNA polymerase, PBS2 phage RNA polymerase, vaccinia virus RNA polymerase, *Escherichia coli* RNA polymerase, and mitochondrion RNA polymerase.

DEFINITIONS

Figure 1:
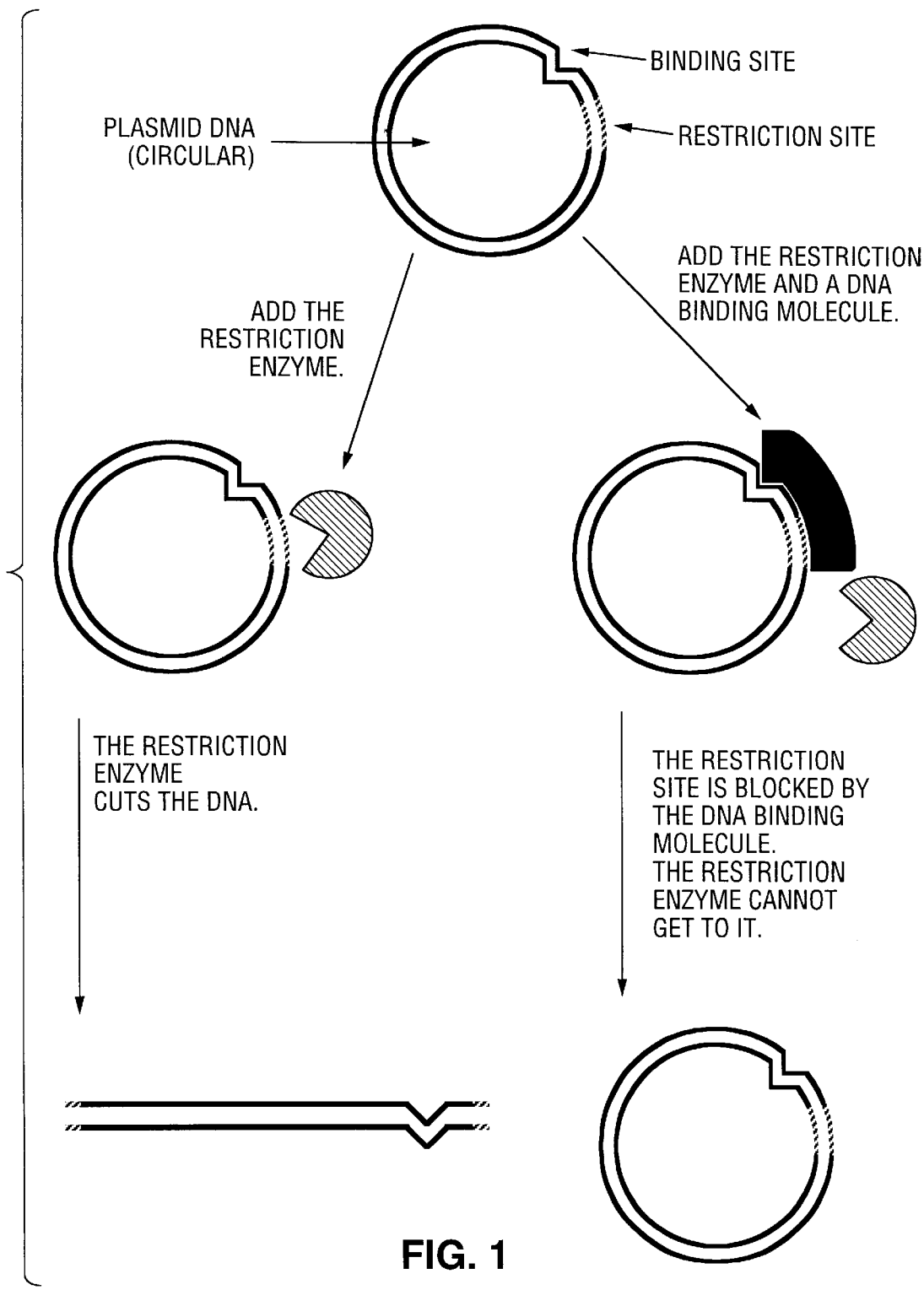
FIG. 1 is a schematic representation of the principles of the methods for detecting the presence and determining the DNA-binding activity of sequence-specific DNA-binding molecules.

To facilitate understanding of the invention, a number of terms are defined below.

The term "recombinant plasmid" as used herein refers to a circular DNA molecule that contains segments of DNA joined together by means of molecular biological techniques.

The terms "specific binding," "binding specificity," and grammatical equivalents thereof when made in reference to a nucleotide sequence and a first molecule refer to the preferential interaction between the nucleotide sequence with the first molecule as compared to the interaction between either of the nucleotide sequence and of the first molecule with a second molecule. Specific binding is a relative term that does not require absolute specificity of binding; in other words, the term "specific binding" does not require that the nucleotide sequence interacts with the first molecule in the absence of an interaction between the nucleotide sequence and the second molecule. It is sufficient that the level of interaction between the nucleotide sequence and the first molecule is greater that the level of interaction between the nucleotide sequence and the second molecule. "Specific binding" of a nucleotide sequence with a first molecule means that the interaction between the nucleotide sequence and the first molecule is dependent upon the presence of a particular structure on or within the nucleotide sequence; in other words the first molecule is recognizing and binding to a specific structure on or within the nucleotide sequence rather than to nucleic acids or to nucleotide sequences in general. For example, if a polypeptide is specific for structure "A" that is on or within a nucleotide sequence, the presence of a nucleic acid sequence containing structure A (or free, unlabelled A) in a reaction containing labelled "A" and the polypeptide will reduce the amount of labelled A bound to the polypeptide.

The term "capable of binding" when made in reference to the interaction between a restriction enzyme and a nucleotide sequence means that the restriction enzyme specifically binds to the nucleotide sequence in the presence of suitable concentration of salts, and suitable temperature, and pH. The conditions for specifically binding a restriction enzyme to a nucleotide sequence for a multitude of commercially available restriction enzymes are provided by the manufacturers of these restriction enzymes.

The term "restriction endonuclease" or "restriction enzyme" refers to a protein that specifically binds to a particular nucleotide sequence (generally, though not necessarily, from 3 to 8 nucleotides) that is on or within a double-stranded DNA (dsDNA) molecule, and whose binding results in cleavage of the DNA molecule at a restriction site. The nucleotide sequence to that a restriction enzyme binds is herein referred to as the "restriction enzyme binding sequence." The terms "restriction site" and "cleavage site" interchangeably refer to the position between two nucleotides at that the restriction enzyme cleaves the DNA molecule. Restriction sites may be located within the restriction enzyme binding sequence (e.g., the restriction sites for EcoRV, EcoRI, SmaI, HindIII, PacI, and NotI). Alternatively, restriction sites may be located substantially adjacent to the restriction enzyme binding sequence (e.g., the restriction sites for BseRI, BsgI, BsmBI, FokI, and SapI).

The term "DNA-binding activity" when made in reference to a molecule as used herein refers to the ability of the molecule to interact with a DNA sequence. "Sequence-specific DNA-binding activity" of a molecule refers to the specific binding of the molecule with a specific DNA sequence.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables). A biological sample suspected of containing a sequence-specific DNA-binding molecule may comprise a cell, tissue extract, body fluid, chromosomes or extrachromosomal elements isolated from a cell, and the like.

DESCRIPTION OF THE INVENTION

The present invention provides compositions and methods for detecting the presence, determining the amount and concentration of sequence-specific DNA-binding molecules, and determining the amount and concentration of compounds that affect the DNA binding activity of a sequence-specific DNA-binding molecule. The invention further provides compositions and methods for detecting the presence of RNA polymerases, for determining the activity of RNA polymerases in initiating transcription, and for determining the presence and activity of compounds that affect initiation of transcription by RNA polymerases. The compositions and methods provided herein are useful in providing rapid, specific, sensitive and quantitative assays for drug screening, diagnosis of disease, and detection of environmental contaminants.

The description of the invention is divided into three sections: (A) genetically engineered plasmids containing a cognate nucleotide recognition sequence and a unique restriction site, (B) methods for detecting, and determining the activity of, sequence-specific DNA-binding molecules, and (C) methods for determining the initiation of transcription activity of RNA polymerases.

A. Genetically engineered plasmids containing a cognate nucleotide recognition sequence and a unique restriction site The present invention provides genetically engineered plasmids that are useful in (a) detecting the presence, and determining the amount and concentration, of sequence-specific DNA-binding molecules, (b) detecting the presence of RNA polymerases, and determining the activity of RNA polymerases in initiating transcription, and (c) screening candidate inhibitors of the binding of sequence-specific DNA-binding molecules with DNA, and inhibitors of transcription initiation.

The plasmids provided herein are contemplated to contain a cognate nucleotide recognition sequence for a sequence-specific DNA-binding molecule. The term "cognate recognition sequence" when made in reference to a nucleotide sequence that binds to a sequence-specific DNA-binding molecule means that the nucleotide sequence is capable of specifically binding to the sequence-specific DNA-binding molecule. It is contemplated that the plasmids of the invention include any cognate nucleotide recognition sequence for any sequence-specific DNA-binding molecule so long as the sequence of the cognate nucleotide recognition sequence is known. The cognate nucleotide recognition sequences for a multitude of molecules are known, and some examples are shown in Table 1.

TABLE 1

Examples of Sequence-Specific DNA-Binding Molecules

| Sequence-Specific DNA-Binding Protein | Organism | Function of the Protein | Cognate DNA-Recognition Sequence |
|---|---|---|---|
| λrepressor | E. coli I | gene repressor | TATCACCGCCAGAGGTA (SEQ ID NO:1) |
| TATA box binding protein | eukaryotes | transcription initiation | GGTATAAAAGG (SEQ ID NO:2) |
| NFκB | mammals | gene activator | GGGAATTCCC (SEQ ID NO:3) |
| Progesterone receptor | mammals | gene regulator activated by progesterone | TGTACANNNTGTTCT (SEQ ID NO:4) |
| Estrogen Receptor | mammals | gene regulator activated by estrogen | AGGAAATTCC (SEQ ID NO:5) |
| Glucocorticoid receptor | mammals | gene regulator activated by | TGTACAGGATGTTCT (SEQ ID NO:6) |

TABLE 1-continued

Examples of Sequence-Specific DNA-Binding Molecules

| Sequence-Specific DNA-Binding Protein | Organism | Function of the Protein | Cognate DNA-Recognition Sequence |
|---|---|---|---|
| | | glucocorticoid hormones | |
| Androgen receptor | mammals | gene regulator activated by testosterone | ATGTACAGGATGTTCT (SEQ ID NO:7) |
| Retinoid receptor family RAR RXR | mammals | gene regulators activated by retinol | GGTTCANNNNNAGTTCA AGGTCAGAGGTCA (SEQ ID NO:8) |
| Thyroid receptor family | mammals | gene regulators activated by thyroid hormones | AGGTCATGACCT (SEQ ID NO:9) |
| Bacterial RNA polymerase holoenzyme | E. coli | transcription lac promoter | TGTTGACAATTAATCCTCC TCGTATAATGTGTGGA (SEQ ID NO:10) |
| P53 | mammals | tumor suppressor | AGACAAGCCT (SEQ ID NO:11) |
| lac suppressor | E. coli | gene suppressor | AATTGTGAGCGGATAACA ATT (SEQ ID NO:12) |
| AraC | E. coli | regulation of arabinose metabolism | CCATTCAGAGAAGAAACC AATTGTCCATAT (SEQ ID NO:13) |
| DnaA | E. coli | initiation of DNA replication | TTATACACA (SEQ ID NO:14) |
| MerR | E. coli | regulation of mercury metabolism | GCTTGACTCCGTACATGA GTACGGAAGTAA (SEQ ID NO:15) |
| ICP4 | Herpes simplex virus | gene activator, necessary for lytic infection | ATCACGCCCCGATCGTCC ACACGGAGCGCGGCTG (SEQ ID NO:16) |
| UL9 | Herpes Simplex virus origin binding protein | Initiation of viral DNA replication | AGCGTTCGCACTTCGTCC (SEQ ID NO:17) |
| c-Myc/c-Max | mammals | gene activators, oncogenes | CACGTC (SEQ ID NO:18) |
| T7 RNA polymerase | T7 bacteriophage | transcription of viral genes | TAATACGACTCAATATAG GGAGA (SEQ ID NO:19) |
| T3 RNA polymerase | T3 bacteriophage | transcription of viral genes | TTTAGGTGACACTATA (SEQ ID NO:20) |
| SP6 RNA polymerase | SP6 bacteriophage | transcription of viral genes | AATTAACCCTCACTAAA (SEQ ID NO:21) |
| RNA polymerase II | Eurkayotic cells | transcription of most protein-encoding genes | various sequences in conjunction with TBP |
| RecBCD | E. coli | recombination complex | GCTGGTGGAGCT (SEQ ID NO:22) |
| γ/δ resolvase | prokaryotes | recombination of transposons | res site (115 bp sequence) |
| λ phage integrase complex | λbacteriophage | Integration of λDNA into the host genome | AAAAAAGCATTGCTTATC AATTTGTTG (SEQ ID NO:23) |
| DNA photolyase | Bacteria, yeast and a variety of animals | repair of UV-induced DNA damage | thymine dimers in DNA |
| Ada protein | E. coli | repair of DNA damage induced by alkylating agents | methylated guanine or thymine in DNA |
| Methylated Ada protein | E. coli | induction of repair genes | AAGCGCA (SEQ ID NO:24) |
| Rag1/Rag2 | mammals | generation of antibody and T-cell receptor diversity | CACAGTG(N)$_{12}$ or $_{34}$ACAAAAACC (SEQ ID NO:25 and 26) |
| c-Jun | mammals | proto-oncogene | TGAGTCA (SEQ ID NO:27) |
| AP2 | vertebrates | controls morphogenesis | GCCNNNGGC (SEQ ID NO:28) |
| SP1 | human | regulator of a variety of promoters including the HIV LTR promoter | GGGCGG (SEQ ID NO:29) |
| TFIIB | eukaryotes | general transcription initiation factor | binds to promoter region after binding of TPB |
| vitamin D receptor (VDR) | mammals | gene regulator activated by vitamin D | |
| AP-I complex c-jun Jun-B Jun-D c-Fos | mammals | These are transcriptional regulators which to DNA as homo- or heterodimers. | TGACTCA (SEQ ID NO:30) |

TABLE 1-continued

Examples of Sequence-Specific DNA-Binding Molecules

| Sequence-Specific DNA-Binding Protein | Organism | Function of the Protein | Cognate DNA-Recognition Sequence |
|---|---|---|---|
| Fos-B | | | |
| Fra-1 | | | |
| Fra-2 | | Involved in control of cell division and cancer. | |
| Sp1 | mammals | gene regulator | GGGGCGGGG (SEQ ID NO:31) |
| CREB family | human | gene regulators bind to DNA as homo- or heterodimers | TGACCTCA (SEQ ID NO:32) |
| CREB-1 | | | |
| CREB-2 | | | |
| ATF-1 | | | |
| ATF-2 | | | |
| ATF-3 | | | |
| ATF-4 | | | |
| C/EBP family | mammals | gene regulators | TTGCGCAA (SEQ ID NO:33) |
| C/EBPα | | | |
| C/EBPβ | | | |
| C/EBPδ | | | |
| CRP 1 | | | |
| Egr family | mammals | gene regulators | GCGGGGGCAGCGGGGGCG (SEQ ID NO:34) |
| Egr-1 | | | |
| Egr-2 | | | |
| Egr-3 | | | |
| WT | | | |
| Ets family | mammals | transcription factors | CAGGAAGT (SEQ ID NO:35) |
| Ets-1 | | | |
| Ets-2 | | | |
| Erg-1 | | | |
| Erg-2 | | | |
| Elk-1 | | | |
| Fli-T | | | |
| PU.1 | | | |
| PEA3 | | | |
| Elf-1 | | | |
| ETV1 | | | |
| ERM | | | |
| Stat family | mammals | gene activators activated by interferons γ, EGF, IL-4, IL-6 | ATTCCTGTAAG (SEQ ID NO:36) |
| Stat1α p91 | | | TTCTGGGAATT (SEQ ID NO:37) |
| Stat2p113 | | | TTTCCCCGAAAT (SEQ ID NO:38) |
| Stat3 | | | TTTCTAGGAATT (SEQ ID NO:39) |
| Stat4 | | | TTTCCCAGAAA (SEQ ID NO:40) |
| Stat5 | | | |
| Stat6 | | | |
| NF-1 family | eukaryotes | transcription factors involved in the regulation of cell division | TGGATTGAAGCCAAT (SEQ ID NO:41) |
| YYI | mammals | gene regulator that targets many genes with repression or activation effects | GCGGCCATC (SEQ ID NO:42) |
| AP-2 factors | mammals | involved in morphogenesis | GCCCGCGG (SEQ ID NO:43) |
| E2F family | mammals | gene regulators involved in tumor suppression | TTCGCGC (SEQ ID NO:44) |
| IRF family | mammals | regulators of interferon α and β genes and of interferon-inducible genes | GAAAATGAAATT (SEQ ID NO:45) |
| MEF-2 | mammals | muscle specific transcription factors | CTA(A/T)$_4$TAG (SEQ ID NOS:46 and 47) |
| Myo-D/Myo-E | mammals | muscle specific transcription factor | CANNTG (SEQ ID NO:48) |
| Oct family | mammals | homeodomain transcription factors that regulate a variety of genes | ATGCAAAT (SEQ ID NO:49) |
| Pit-1 | mammals | transcription factor similar to Oct-1 | CTGAATATGAATAA (SEQ ID NO:50) |
| USF-1/USF-2 | mammals | ubiquitous transcription factors related to c-myc | CACGTG (SEQ ID NO:51) |
| c-Myb | vertebrates | proto-oncogene | TAACGGTT (SEQ ID NO:52) |

TABLE 1-continued

Examples of Sequence-Specific DNA-Binding Molecules

| Sequence-Specific DNA-Binding Protein | Organism | Function of the Protein | Cognate DNA-Recognition Sequence |
|---|---|---|---|
| Pbx-1 | human | homeobox protein involved in some forms of leukemia | TGATTGAT (SEQ ID NO:53) |
| GATA family | mammals | regulators of erythroid-specific genes and other genes | TGATAANNNNNNNTGATAA (SEQ ID NO:54) |
| NF-E2 | mammals | regulator of erythroid bell differentiation | TGCTGAGTCA (SEQ ID NO:55) |
| Serum response factor | mammals | involved in cell growth stimulation | CCATATTAGG (SEQ ID NO:56) |

In one embodiment, the cognate nucleotide recognition sequence used is that for NFκB. In another embodiment, the cognate nucleotide recognition sequence is one to that *Escherichia coli* RNA polymerase specifically binds. In yet another embodiment, the cognate nucleotide recognition sequence is the sequence to that TBP binds. In a further embodiment, the cognate nucleotide recognition sequence is one to that the λ cI repressor binds.

The plasmids of the invention are contemplated to include one or more unique restriction sites. The term "unique restriction site" when made in reference to a restriction site that is contained within a plasmid that also contains a cognate nucleotide recognition sequence for a sequence-specific DNA-binding molecule means that the restriction site is located on the plasmid at a location such that it is within, or substantially adjacent to, the cognate nucleotide recognition sequence and is not at any other position on the plasmid. Without limiting the invention to any particular mechanism, it is the inventors' view that binding of the sequence-specific DNA-binding molecule to its one or more cognate nucleotide recognition sequences results in "protection" of the one or more restriction sites from cleavage by the restriction enzyme.

Figure 4A:
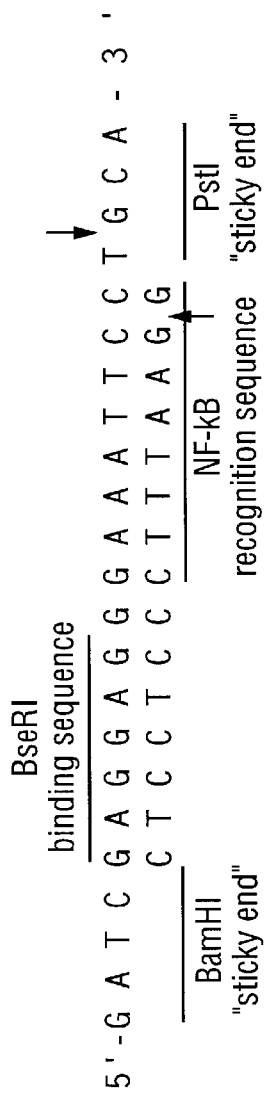
FIG. 4 shows the oligonucleotide sequences containing a unique restriction enzyme cleavage site and the cognate nucleotide recognition sequences for (a) NF-κB, (SEQ ID NOS: 63 and 68) (b) TATA binding protein (SEQ ID NOS: 64 and 69); (c) lambda cI repressor protein (SEQ ID NOS: 66 and 70); and (d) RNA polymerase (SEQ ID NOS: 71 and 72). Overlined regions of the sequences indicate restriction enzyme binding sequences and underlined regions are sequence-specific DNA-binding protein recognition sequences. Arrows indicate the points of restriction enzyme cleavage.
Figure 4B:
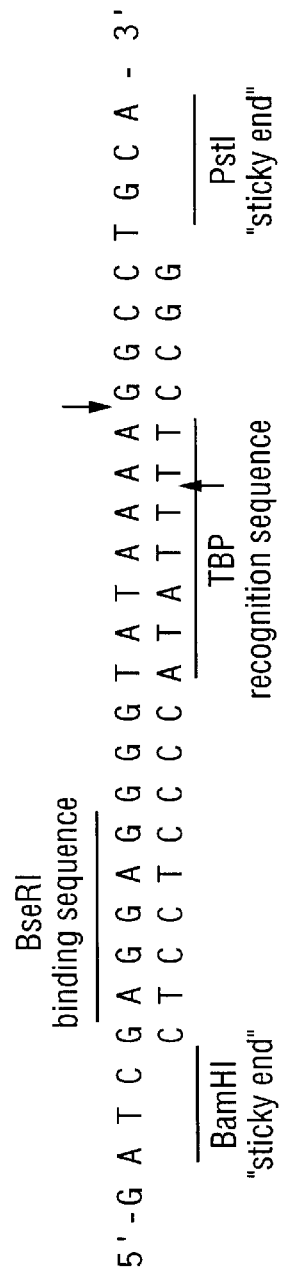
Figure 4C:
Figure 4D:
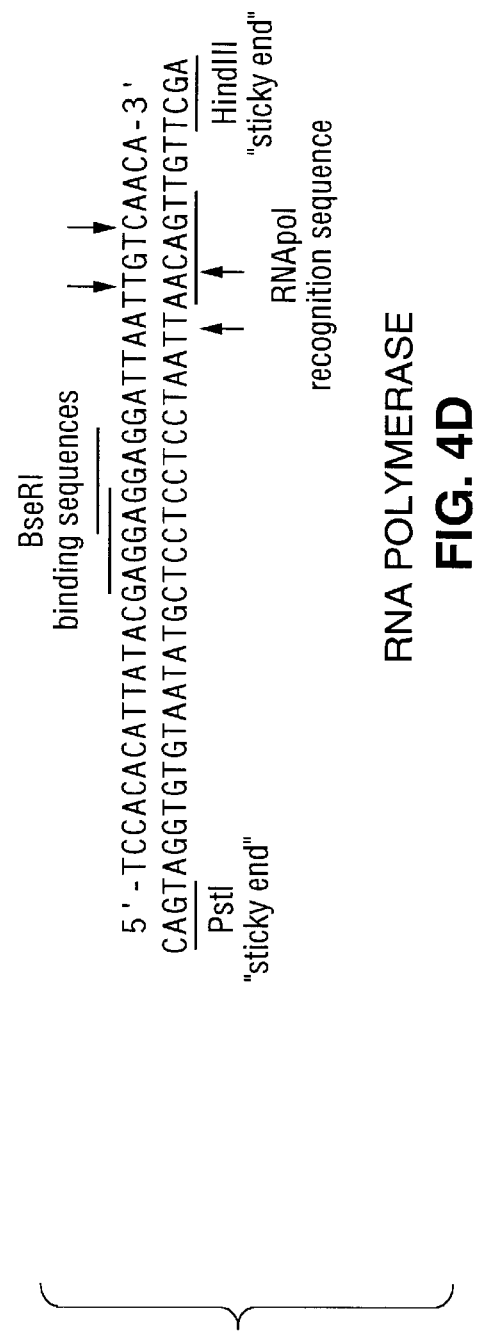

The term "located within" when made in reference to a restriction site as it relates to a sequence-specific DNA-binding molecule's cognate nucleotide recognition sequence as used herein means that the position at that the restriction enzyme cleaves is between two nucleotide bases that are part of the cognate nucleotide recognition sequence. For example, the restriction site of the restriction enzyme BseRI is within the cognate nucleotide recognition sequence of the NFκB protein in plasmid pDNAB-NFκB (FIG. 4A), and is within the cognate nucleotide recognition sequence of the TBP protein in plasmid pDNAB-TATA (FIG. 4B). In another example, one of the restriction sites of the restriction enzyme BseRI is within the cognate nucleotide recognition sequence of *Escherichia coli* RNA polymerase (FIG. 4D). In yet another example, the restriction site of the restriction enzyme EcoRV is within the cognate nucleotide recognition sequence of the λ cI repressor protein in plasmid pDNAB-orl (FIG. 4C).

In contrast, as used herein, the term "substantially adjacent" when made in reference to a restriction site as it relates to a sequence-specific DNA-binding molecule's cognate nucleotide recognition sequence means that the position at that the restriction enzyme cleaves is between two nucleotide bases that are not part of the cognate nucleotide recognition sequence, and that the position at that the restriction enzyme cleaves is located preferably from 1 to 100, more preferably from 1 to 50, and most preferably from 1 to 10 nucleotide bases either downstream or upstream of the cognate nucleotide recognition sequence. The term "substantially adjacent" when made in reference to a restriction site as it relates to a sequence-specific DNA-binding molecule's cognate nucleotide recognition sequence also means that, in the presence of the sequence-specific DNA-binding molecule, a DNA molecule that contains the restriction site at a position substantially adjacent to the sequence-specific DNA-binding molecule's cognate nucleotide recognition sequence is not substantially cleaved by the restriction enzyme at the restriction site.

The present invention contemplates plasmids wherein the molecular footprint of a sequence-specific DNA-binding molecule covers a region of the plasmid nucleic acid that encompasses a restriction site, thereby blocking access of the restriction enzyme and inhibiting cleavage oat the site. In order to cover the restriction site, the restriction site must necessarily be "substantially adjacent" to the cognate nucleotide recognition sequences for the sequence-specific DNA-binding molecule, ie., be either within the cognate nucleotide recognition sequence or sufficiently adjacent thereto such that cleavage by the restriction enzyme is inhibited.

The term "not substantially cleaved" when made in reference to a DNA molecule (e.g., plasmid) containing a restriction site and a sequence-specific DNA-binding molecule's cognate nucleotide recognition sequence is a relative term that means that the level of cleavage of the DNA molecule in the presence of the sequence-specific DNA-binding molecule is reduced relative to the level of cleavage of the DNA molecule in the absence of the sequence-specific DNA-binding molecule. In other words, the level of cleavage of the DNA molecule in the presence of the sequence-specific DNA-binding molecule is less than the level of cleavage in the absence of the sequence-specific DNA-binding molecule, preferably at least 10% less than the level of cleavage in the absence of the sequence-specific DNA-binding molecule, more preferably at least 50% less than the level of cleavage in the absence of the sequence-specific DNA-binding molecule, yet more preferably at least 90% less than the level of cleavage in the absence of the sequence-specific DNA-binding molecule, and most preferably is at the background level of, or is undetectable by, florescence when molecules (e.g., ethidium bromide) that intercalate into double-stranded DNA are used as described herein. When a background level or undetectable level of cleavage is measured, this may indicate that the DNA molecule containing the restriction site and the sequence-specific DNA-binding molecule's cognate nucleotide recognition sequence is not cleaved. The term "not substantially cleaved" need not, although it may, mean an absolute absence of cleavage of the DNA molecule. The invention does not require, and is not limited to DNA molecules that are 100% not cleaved by the restriction enzyme.

Figure 5:
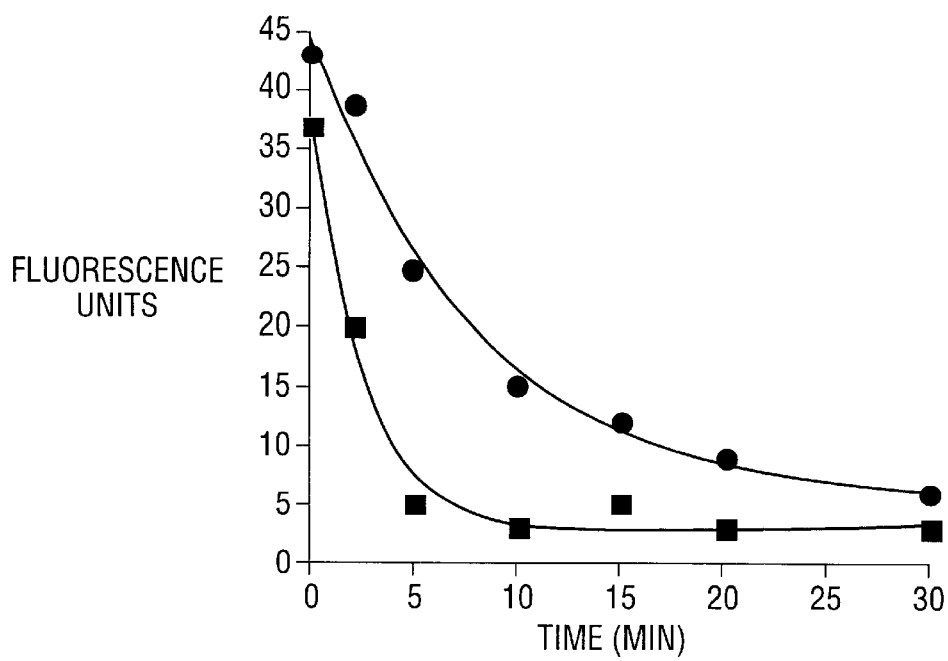
FIG. 5 shows a time course of digestion by BseRI of the plasmid pDNAB-NFκB in the absence (squares) or presence (circles) of 6 ng/μL of NFκB.
Figure 6:
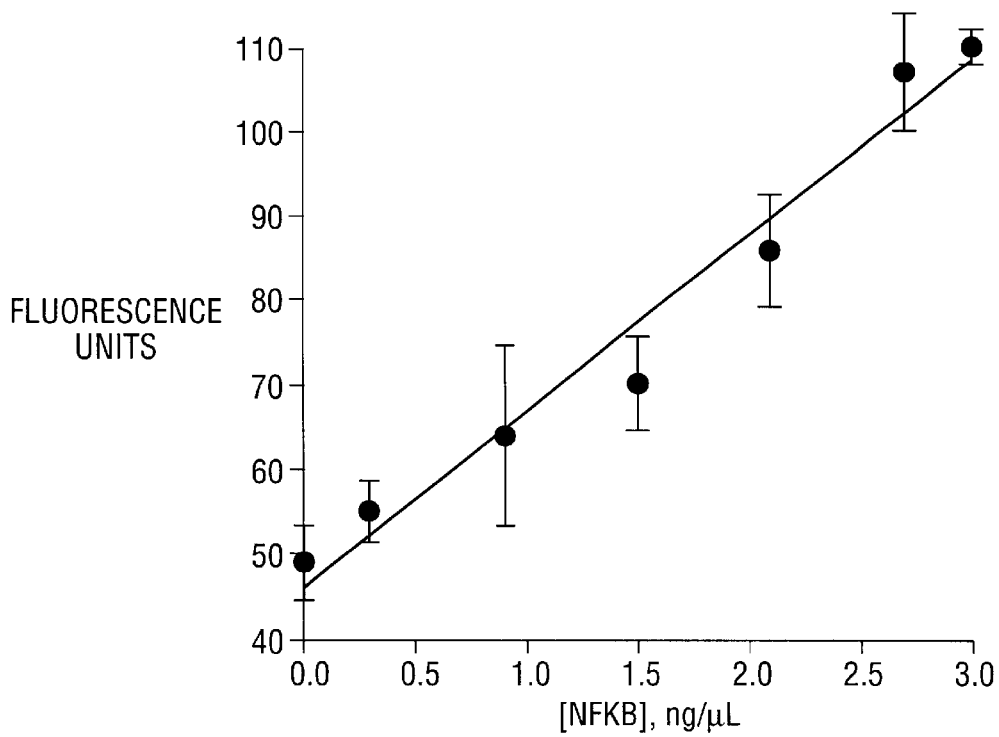
FIG. 6 is a graph showing quantitation of NFκB DNA-binding activity.
Figure 13:
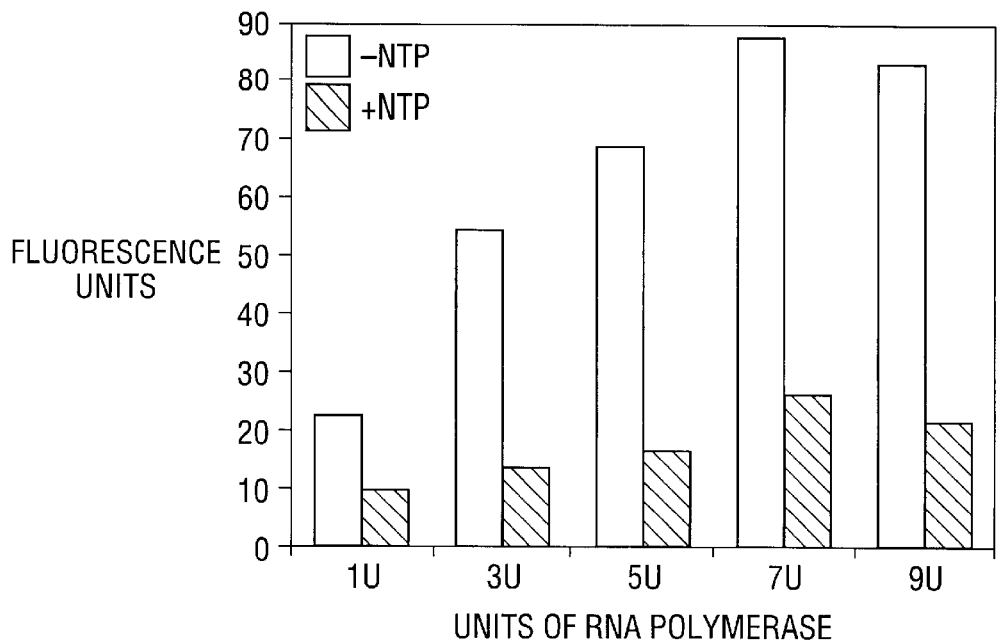
FIG. 13 is a bar graph showing the detection of the transcription initiation activity of *E. coli* RNA polymerase.

For example, data presented herein demonstrates that increasing amounts of RNA polymerase, an exemplary sequence-specific DNA binding molecule, provide increasing levels of protection of the plasmids of the invention from cleavage by restriction enzymes (FIG. 13). The invention further demonstrates (FIG. 5) that the presence of NFκB reduces the rate of cleavage in a quantitative manner as shown in FIG. 6, yet does not prevent cleavage if incubation is prolonged for 30 minutes or more.

In addition to containing a restriction site(s) within or substantially adjacent to a sequence-specific DNA-binding molecule's cognate nucleotide recognition sequence, the plasmids provided herein are contemplated also to contain a restriction enzyme binding sequence. The invention expressly contemplates plasmids that contain restriction sites and restriction enzyme binding sequences for any restriction enzyme whose restriction site is within or substantially adjacent to the restriction enzyme binding sequence.

The term "located within" when made in reference to a restriction site as it relates to restriction enzyme binding sequence as used herein means that the position at that the restriction enzyme cleaves is between two nucleotide bases that are part of the restriction enzyme binding sequence. For example, the restriction site of the restriction enzyme EcoRV is within EcoRV's binding sequence (FIG. 4C). Other commercially available restriction enzymes whose restriction sites are located within their binding sequence are known in the art such as those described in Table 2. The restriction enzymes in Tables 2–4 are commercially available from one or more of New England Biolabs (Beverly, Mass.), Boehringer-Mannheim (Mannheim, Germany), and Life Technologies Inc. (Gaithersburg, Md.).

TABLE 2

Examples of Restriction Enzymes That Cleave DNA Within Their Binding Sequence

| Name | Binding Sequence[a] |
|---|---|
| Aat II | GACGT/C |
| Acc I | GT/MKAC |
| Afl II | C/TTAAG |
| Afl III | A/CRYGT |
| Aha II | GR/CGYC |
| Alu I | AG/CT |
| AlwN I | CAGNNN/CTG |
| Apa I | GGGCC/C |
| ApaL I | G/TGCAC |
| Ase I | AT/TAAT |
| Asp718 | G/GTACC |
| Ava I | C/YCGRG |
| Ava II | G/GWCC |
| Avr II | C/CTAGG |
| Bal I | TGG/CCA |
| BamH I | G/GATCC |
| Ban I | G/GYRCC |
| Ban II | GRGCY/C |
| Bbe I | GGCGC/C |
| Bcl I | T/GATCA |
| Bcn I | CCS/GG |
| Bgl I | GCCNNNN/NGGC (SEQ ID NO:57) |
| Bgl II | A/GATCT |
| Bsp1286 I | GDGCH/C |
| BspH I | T/CATGA |
| BspM II | T/CCGGA |
| BssH II | G/CGCGC |
| BstB I | TT/CGAA |
| BstE II | G/GTNACC |
| BstN I | CC/WGG |
| BstU I | CG/CG |
| BstX I | CCANNNNN/NTGG (SEQ ID NO:58) |
| BstY I | R/GATCY |
| Bsu36 I | CC/TNAGG |
| Cfr10 I | R/CCGGY |
| Cla I | AT/CGAT |
| Dde I | C/TNAG |
| Dpn I | GA/TC |
| Dra I | TTT/AAA |
| Dra III | CACNNN/GTG |
| Eae I | Y/GGCCR |
| Eag I | C/GGCCG |
| Eco47 III | AGC/GCT |
| EcoN I | CCTNN/NNNAGG (SEQ ID NO:59) |
| EcoO109 I | RG/GNCCY |
| EcoR I | G/AATTC |
| EcoR II | /CCWGG |
| EcoR V | GAT/ATC |
| Esp I | GC/TNAGC |
| Fnu4H I | GC/NGC |
| Fsp I | TGC/GCA |
| Hae I | WGG/CCW |

TABLE 2-continued
Examples of Restriction Enzymes That Cleave DNA Within Their Binding Sequence

| Name | Binding Sequence[a] |
|---|---|
| Hae II | RGCGC/Y |
| Hae III | GG/CC |
| HgiA I | GWGCW/C |
| Hha I | GCG/C |
| HinC II | GTY/RAC |
| HinD III | A/AGCTT |
| Hinf I | G/ANTC |
| HinP I | G/CGC |
| Hpa I | GTT/AAC |
| Hpa II | C/CGG |
| Kpn I | GGTAC/C |
| Mae I | C/TAG |
| Mae II | A/CGT |
| Mae III | /GTNAC |
| Mbo I | /GATC |
| Mlu I | A/CGCGT |
| Mse I | T/TAA |
| Msp I | C/CGG |
| Nae I | GCC/GGC |
| Nar I | GG/CGCC |
| Nci I | CC/SGG |
| Nco I | C/CATGG |
| Nde I | CA/TATG |
| Nhe I | G/CTAGC |
| Nla III | CATG/ |
| Nla IV | GGN/NCC |
| Not I | GC/GGCCGC |
| Nru I | TCG/CGA |
| Nsi I | ATGCA/T |
| Nsp7524 I | R/CATGY |
| NspB II | CMG/CKG |
| NspH I | RCATG/Y |
| PaeR7 I | C/TCGAG |
| PflM I | CCANNNN/NTGG (SEQ ID NO:60) |
| PpuM I | RG/GWCCY |
| Pst I | CTGCA/G |
| Pvu I | CGAT/CG |
| Pvu II | CAG/CTG |
| Rsa I | GT/AC |
| RsrII | CG/GWCCG |
| Sac I | GAGCT/C |
| Sac II | CCGC/GG |
| Sal I | G/TCGAC |
| Sau3A I | /GATC |
| Sau96 I | G/GNCC |
| Sca I | AGT/ACT |
| ScrF I | CC/NGG |
| Sec I | C/CNNGG |
| Sfi I | GGCCNNNN/NGGCC (SEQ ID NO:61) |
| Sma I | CCC/GGG |
| SnaB I | TAC/GTA |
| Spe I | A/CTAGT |
| Sph I | GCATG/C |
| Spl I | C/GTACG |
| Ssp I | AAT/ATT |
| Stu I | AGG/CCT |
| Sty I | C/CWWGG |
| Taq I | T/CGA |
| Tth111 I | GACN/NNGTC |
| Xba I | T/CTAGA |
| Xca I | GTA/TAC |
| Xho I | C/TCGAG |
| Xma I | C/CCGGG |
| Xmn I | GAANN/NNTTC (SEQ ID NO:62) |

[a] Only the strand in the 5' to 3' direction is shown. The character '/' indicates the position of the cleavage site. N indicates any nucleotide; R indicates A or G; Y indicates C or T; M indicates A or C; K indicates G or T; S indicates C or G; W indicates A or T; H indicates A or C or T; B indicates C or G or T; V indicates A or C or G; D indicates A or G or T.

The term "substantially adjacent" when made in reference to a restriction site as it relates to a restriction enzyme binding sequence means that the position at that the restriction enzyme cleaves is between two nucleotide bases that are not part of the restriction enzyme binding sequence, and that the position at that the restriction enzyme cleaves is located preferably from 1 to 50, more preferably from 1 to 30, and most preferably from 1 to 10 nucleotide bases either downstream or upstream of the restriction enzyme binding sequence. In one embodiment, the plasmid contains the binding sequence and restriction site for the restriction enzyme BseRI in that the BseRI restriction site is located 10 nucleotides downstream of the 5' end of the BseRI binding sequence (FIG. 4A, B, and D). Other enzymes whose restriction site is substantially adjacent to their binding sequence are known in the art such as those listed in Table 3.

TABLE 3

Examples of Restriction Enzymes That Cleave DNA Outside Of Their Binding Sequence

| Name | Binding Sequence[a] | | |
|---|---|---|---|
| AlwI | GGATC | 4 | 5 |
| Bbv I | GCAGC | 8 | 12 |
| Bbv II | GAAGAC | 2 | 6 |
| BseRI | GAGGAG | 10 | 8 |
| Bsm I | GAATGC | 1 | -1 |
| BsmA I | GTCTC | 1 | 5 |
| BspM I | ACCTGC | 4 | 8 |
| Bsr I | ACTGG | 1 | -1 |
| Ear I | CTCTTC | 1 | 4 |
| Fok I | GGATG | 9 | 13 |
| Gdi II | YGGCCG | -5 | -1 |
| Hga I | GACGC | 5 | 10 |
| Hph I | GGTGA | 8 | 7 |
| Mbo II | GAAGA | 8 | 7 |
| Mnl I | CCTC | 7 | 7 |
| Ple I | GAGTC | 4 | 5 |
| SfaN I | GCATC | 5 | 9 |
| Tth111 II | CAARCA | 11 | 9 |

[a]Only the strand in the 5' to 3' direction is shown. The two numbers next to the binding sequence indicate the number of nucleotides that are adjacent to the binding sequence and at that the enzyme cleaves at the cleavage site on the 5' to 3' strand (first number) and on the complementary strand (second number). N indicates any nucleotide; R indicates A or G; Y indicates C or T; M indicates A or C; K indicates G or T; S indicates C or G; W indicates A or T; H indicates A or C or T; B indicates C or G or T; V indicates A or C or G; D indicates A or G or T.

While the preferred embodiment uses plasmids that contain the restriction binding sequence and restriction site for the exemplary restriction enzymes BseRI and EcoRV, the plasmids of the invention are not limited to plasmids containing the herein disclosed restriction enzyme binding sequences or restriction sites. Any restriction enzyme binding sequence and any restriction site for any restriction enzyme is contemplated to be within the scope of the invention so long as the restriction enzyme binding sequence and/or the restriction site are placed in such a position with respect to the cognate nucleotide recognition sequence of a sequence-specific DNA-binding molecule such that the plasmid is not substantially cleaved when the sequence-specific DNA-binding molecule binds to its cognate nucleotide recognition sequence. Binding sequences and restriction sites for numerous commercially available restriction enzymes are known in the art including, but not limited to, those described in Tables 2 and 3.

The plasmids of the invention are contemplated to contain a restriction enzyme binding sequence that is located within, overlaps with, or is substantially adjacent to, a sequence-specific DNA-binding molecules cognate nucleotide recognition sequence.

The term "located within" when made in reference to a restriction enzyme binding sequence as it relates to a sequence-specific DNA-binding molecule's cognate nucleotide recognition sequence as used herein means that the entire restriction enzyme binding sequence is the same as the entire, or a portion of, the sequence-specific DNA-binding molecule's cognate nucleotide recognition sequence, and is contained within the sequence-specific DNA-binding molecule's cognate nucleotide recognition sequence.

On the other hand, the term "overlaps with" when made in reference to a restriction enzyme binding sequence as it relates to a sequence-specific DNA-binding molecule's cognate nucleotide recognition sequence as used herein means that at least one, but less than all, of the nucleotides of the restriction enzyme binding sequence and of the sequence-specific DNA-binding molecule's cognate nucleotide recognition sequence are the same. In one embodiment, the BseRI binding sequence overlaps by one nucleotide with the NF-κB cognate nucleotide recognition sequence (FIG. 4A). In another embodiment the BseRI binding sequence overlaps by four nucleotides with the λ cI repressor cognate nucleotide recognition sequence (FIG. 4C).

The term "substantially adjacent" when in reference to a restriction enzyme binding sequence as it relates to a sequence-specific DNA-binding molecule's cognate nucleotide recognition sequence means that the restriction enzyme binding sequence is separated from the sequence-specific DNA-binding molecule's cognate nucleotide recognition sequence by, preferably from 1 to 500 nucleotides, more preferably from 1 to 100 nucleotides, and most preferably from 1 to 30 nucleotides. In one embodiment, BseRI binding sequence is separated by 3 nucleotides from the TBP cognate nucleotide recognition sequence (FIG. 4B). In another embodiment, the BseRI binding sequence is separated by 6 nucleotides from the RNA polymerase cognate nucleotide recognition sequence (FIG. 4D).

The present invention contemplates plasmids with one or more restriction enzyme binding sequences and/or one or more restriction sites so long as the one or more restriction enzyme binding sequences and/or the one or more restriction sites are placed in such a position with respect to the cognate nucleotide recognition sequence of a sequence-specific DNA-binding molecule such that the plasmid is not substantially cleaved when the sequence-specific DNA-binding molecule binds to its cognate nucleotide recognition sequence. In one embodiment, the plasmid contains two restriction enzyme binding sequences and two restriction sites (FIG. 4D). In another embodiment the plasmid contains one restriction enzyme binding sequence and one restriction site (FIG. 4A, B, and C).

Also within the scope of the invention are plasmids that contain two or more cognate nucleotide recognition sequences for one sequence-specific DNA-binding molecule as well as contain one restriction site for one restriction enzyme, where the sequence of the two or more cognate nucleotide recognition sequences is the same. Such plasmids are desirable where, for example, binding of the sequence-specific DNA-binding molecule (e.g., estrogen receptor) is enhanced by the presence of two or more cognate nucleotide recognition sequences. The two or more cognate nucleotide recognition sequences may be directly (ie., in the absence of intervening nucleotides) or indirectly (i.e., in the presence of intervening nucleotides) ligated. Placing the single restriction site within, or substantially adjacent to, one of the sequence-specific DNA-binding molecule's cognate nucleotide recognition sequences has the advantage of increasing the sensitivity of detecting and quantitating sequence-specific DNA-binding molecules whose binding to their cognate nucleotide recognition sequence is enhanced by the presence of more than one cognate nucleotide recognition sequence.

The invention also includes within its scope plasmids that contain two or more cognate nucleotide recognition sequences for one sequence-specific DNA-binding molecule as well as contain more than one restriction site for a single restriction enzyme, where the sequence of the two or more cognate nucleotide recognition sequences is the same. In a preferred embodiment, at least one restriction site is located within (or substantially adjacent to) each of the cognate nucleotide recognition sequences. This arrangement requires that all the restriction sites on the plasmid are protected by binding of the sequence-specific DNA-binding molecule to its cognate nucleotide recognition sequence in order to prevent cutting. Such plasmids are desirable to increase the sensitivity of detection and/or quantitation of inhibitors of the binding of sequence-specific DNA-binding molecules to their cognate nucleotide recognition sequences. For example, in a first assay where a plasmid contains one cognate nucleotide recognition sequence and one restriction site, and where sufficient sequence-specific DNA-binding molecule is added to occupy 50% of the cognate nucleotide recognition sequence, it is expected by the inventors that 50% of the plasmid molecules will be protected from cutting. In a second assay where the plasmid carries two cognate nucleotide recognition sequences and two restriction sites, both sites must be protected in order to prevent cutting; the probability of this happening is expected by the inventors to be 0.5×0.5=0.25, or 25%. In other words, only 25% of the plasmid molecules will be protected from cutting, although the DNA-binding molecule is bound to 50% of the available sites. Therefore, the second assay will be less sensitive than the first assay in measuring binding of the sequence-specific DNA-binding molecule to its cognate nucleotide recognition sequences, since more of the DNA-binding molecule will be needed in the second assay to provide the same level of protection of the plasmid as in the first assay. On the other hand, detection of inhibitors of binding will be more sensitive in the second assay, because the binding of fewer sequence-specific DNA-binding molecules needs to be inhibited in order to de-protect at least one restriction site on the plasmid.

The invention further contemplates plasmids that contain two or more cognate nucleotide recognition sequences for more than one sequence-specific DNA-binding molecule as well as contain more than one restriction site for different restriction enzymes, where the sequence of the two or more cognate nucleotide recognition sequences is different. In a preferred embodiment, the two restriction sites for the different restriction enzymes are placed within (or substantially adjacent to) the different sequences-specific DNA-binding molecule's cognate nucleotide recognition sequences. Such plasmids may be desirable to, for example, detect and/or quantitate two or more sequence-specific DNA-binding molecules. To illustrate, a plasmid may carry a restriction site for EcoRV within the cognate nucleotide recognition sequence for the λ cI repressor, as well as carry a BseRI restriction site within the cognate nucleotide recognition sequence for NFκB. Plasmids such as these could be used as polyvalent reagents to assay more than one type of sequence-specific DNA-binding molecule in a single test sample.

Also included within the scope of the invention are plasmids that contain two or more cognate nucleotide recognition sequences for more than one sequence-specific DNA-binding molecule as well as contain more than one restriction site for a particular restriction enzyme, where the sequence of the two or more cognate nucleotide recognition sequences is different. In a preferred embodiment, the two restriction sites for the same restriction enzyme are placed within (or substantially adjacent to) the two or more cognate nucleotide recognition sequences for the two or more different sequence-specific DNA-binding molecules. Such plasmids are useful to detect and/or quantitate the simultaneous binding of two different sequence-specific DNA-binding molecules to their respective cognate nucleotide recognition sequences.

The invention further includes within its scope plasmids that contain two or more cognate nucleotide recognition sequences for more than one sequence-specific DNA-binding molecule as well as contain a single restriction site for a particular restriction enzyme, where the sequence of the two or more cognate nucleotide recognition sequences is different, and where the single restriction site is located within (or substantially adjacent to) only one of the cognate nucleotide recognition sequences. For example, a plasmid may carry the cognate nucleotide recognition sequence for the estrogen receptor with a BseRI restriction site placed within (or substantially adjacent to) it, as well as contain the cognate nucleotide recognition sequence for NFκB, in the absence of a restriction site near the NFκB cognate nucleotide recognition sequence. Such plasmids are desirable to, for example, detect and/or quantitate interactions among sequence-specific DNA-binding molecules (e.g., whether the binding of NFκB to its cognate nucleotide recognition sequence is required for the binding of the estrogen receptor to its cognate nucleotide recognition sequence).

The plasmids of the invention are not limited to the source or nature of the backbone into that the restriction enzyme binding sequence, the unique restriction site, and the cognate nucleotide recognition sequence are introduced so long as the plasmid is capable of replicating in a host cell. Such plasmids are commercially available and include, but are not limited to those described in the following Table 4.

TABLE 4

Exemplary Plasmids

| Plasmid | Size | Host Organism | GenBank Accession No. |
|---|---|---|---|
| pUC19 | 2.7 kb | E. coli | X02514 |
| pBR322 | 4.4 kb | E. coli | J01749 |
| SV40 | 5.2 kb | mammalian cells | J02400 |
| YEp24 | 7.8 kb | S. cerevisiae E. coli | L09156 |
| pSV-SPORT | 3.2 kb | E. coli mammalian cells | U14626 |
| pSFV1 | 11.0 kb | E. coli mammalian cells | Patent # WO 9210578 and Vector DATA base #IG9000 |

Many more plasmids are commercially available and can be constructed by adding and removing fragments of DNA from existing plasmids. Restriction enzyme binding sequences, restriction sites, and cognate nucleotide recognition sequences may be introduced into any plasmid using routine molecular biological techniques. One of skill in the art knows that while a relatively large plasmid (e.g., approximately 10–100 kb) increases the sensitivity of the assay (a greater loss of fluorescence per restriction enzyme cut), a relatively small size plasmid (e.g., approximately 2–5 kb) is easier to produce in pure covalently closed circular (ccc) DNA form that is a desirable form for the methods of the invention particularly when using dyes that intercalate into double-stranded DNA; cccDNA is double-stranded and allows intercalation of the dyes and detection of cleavage and linearization of the cccDNA. Additionally, one of skill in the art appreciates that it is desirable to use plasmids that are capable of replicating in different types of host cells to, for example, clone those cognate nucleotide recognition sequences that may be mutated or deleted in *Escherichia coli*.

B. Methods for detecting, and determining the activity of sequence-specific DNA-binding molecules The present invention provides methods for detecting, as well as for determining the activity of, sequence-specific DNA-binding molecules. The methods of the invention not only are capable of detecting the presence of sequence-specific DNA-binding molecules, but also provide a quantitative, rapid, specific, sensitive and reliable measure of the DNA-binding activity of these molecules. These advantages are valuable in using the methods of the invention for screening chemical libraries for candidate therapeutic drugs. Thus, while currently available techniques for drug screening include time consuming and laborious approaches such as electrophoresis coupled with Western blotting, gel retardation assays using radioactive oligonucleotides, and functional assays in vitro or in vivo, the methods of the invention provide data within minutes, may be automated to increase throughput, and do not require the use of radioactive isotopes.

For example, the methods provided herein may be used to screen candidate molecules that alter the activity or amount of sequence-specific DNA-binding molecules. Examples of such molecules include those that target anti-estrogen receptors in treating breast cancer, anti-androgen receptors in treating prostate cancer, and anti-cancer drugs targeted to gene activators such as NFκB and p53.

Yet another example involves the use of the methods of the invention to provide a specific and sensitive assay for detecting steroids (that bind to sequence-specific DNA-binding steroid receptors) e.g., in the blood and urine of athletic competitors.

A further example of the utility of the methods provided herein includes screening potential antibiotics that target bacterial RNA polymerases (e.g., Example 4). This utility is particularly important as more and more traditional antibiotics become less useful as a result of the multiple-drug resistance of bacteria.

The methods provided herein are also useful in the diagnosis, and in determining the prognosis, of any disease that is associated with changed (ie., increased or decreased) levels of DNA-binding activity of a sequence-specific DNA-binding molecule. For example, where a sequence-specific DNA-binding molecule is associated with a disease state, detection of the presence, and/or quantitation of the DNA-binding activity, of the sequence-specific DNA-binding molecule would aid the practitioner in detecting the disease and determining prognosis. For example, some types of cancer have increased levels of c-myc, or have mutations that inactivate p53. Detection and/or quantitation of factor p53 and c-myc using the methods provided herein is useful in detecting these cancers and in determining the patients' prognosis. Additionally, the methods of the invention allow rational determination of the type of drug to be used in therapy. For example, if a disease is found to be associated with the presence (and/or particular DNA-binding activity levels) of a sequence-specific DNA-binding molecule, then a promising therapeutic regimen would involve selection of a drug that inhibits DNA binding by the sequence-specific DNA-binding molecule. To illustrate, the methods of the invention may be used to determine the DNA-binding activity of estrogen receptors in breast cancer tissue, of androgen receptors in prostate cancer tissue, and of p53 and c-myc in other cancerous tissue, for the purpose of diagnosing the presence of the cancer, of determining the patient's prognosis, and of determining the type of anti-cancer drug to be used.

For clarity, this section is further divided into (1) Sequence-specific DNA-binding molecules, (2) Cognate nucleotide recognition sequences, and (3) Detecting the presence, and determining the activity, of sequence-specific DNA-binding molecules.

1. Sequence-specific DNA-binding molecules

The methods provided herein are useful in detecting the presence, as well as determining the activity, of any sequence-specific DNA-binding molecule. Sequence-specific DNA-binding molecules are exemplified by nucleic acid sequences that contain nucleic acids and/or nucleic acid derivatives. Nucleic acid sequences include DNA sequences (e.g., genomic DNA, cDNA, etc.), and RNA sequences (e.g., antisense sequences, ribozymes, etc.). The term "derivative" when used in reference to a nucleic acid refers to the chemical modification of the nucleic acid. Illustrative of such modifications would be replacement of hydrogen by an alkyl, acyl, or amino group. Derivative nucleic acids are illustrated by peptide nucleic acids (PNA), 2'-O-methyl RNAs, and phosphorothiolate DNAs. The term "derivative" when in reference to a nucleotide sequence means that the nucleotide sequence contains at least one derivative nucleic acid.

Sequence-specific DNA-binding molecules also include amino acid sequences (e.g., polypeptides and proteins) that contain amino acids and/or amino acid derivatives. A "derivative" of an amino acid is a chemically modified amino acid. Illustrative of such modifications would be replacement of hydrogen by an alkyl, acyl, or amino group, or formation of covalent adducts with biotin or fluorescent groups. Amino acids include biological amino acids as well as non-biological amino acids. The term "biological amino acid" refers to any one of the known 20 coded amino acids that a cell is capable of introducing into a polypeptide translated from an mRNA. The term "non-biological amino acid" refers to an amino acid that is not a biological amino acid. Non-biological amino acids are useful, for example, because of their stereochemistry or their chemical properties. The non-biological amino acid norleucine, for example, has a side chain similar in shape to that of methionine. However, because it lacks a side chain sulfur atom, norleucine is less susceptible to oxidation than methionine. Other examples of non-biological amino acids include aminobutyric acids, norvaline and allo-isoleucine, that contain hydrophobic side chains with different steric properties as compared to biological amino acids. The term "derivative" when in reference to an amino acid sequence means that the amino acid sequence contains at least one derivative amino acid.

In a preferred embodiment, the sequence-specific DNA-binding molecule is a protein. Sequence-specific DNA-binding proteins are known to have one or more cognate nucleotide recognition sequences. Exemplary sequence-specific DNA-binding proteins and one of their known cognate nucleotide recognition sequences are illustrated by, but not restricted to, those listed in Table 1, supra.

Sequence-specific DNA-binding proteins contemplated to be within the scope of this invention include, but are not limited to, proteins consisting of a single polypeptide chain (e.g., the bacterial lac repressor, the bacterial mercury repressor, TATA box binding protein, T7 RNA polymerase, HSV-1 ICP4, etc.). Alternatively, the sequence-specific DNA-binding proteins may contain two or more polypeptide chains in that the polypeptide chains have the same amino acid sequence (e.g., DnaA, NFκB, steroid receptors, homeodomain proteins, etc.) or different amino acid sequences (e.g., bacterial RNA polymerase, eukaryotic RNA polymerases, eukaryotic origin binding complexes, c-Myc/c-Max, etc.).

Sequence-specific DNA-binding proteins are contemplated to have one or more functions including, for example, DNA transcription, DNA replication, DNA recombination and DNA repair. Sequence specific DNA-binding proteins that function in DNA transcription include, for example, gene repressors (e.g. mercury repressor, LacI, steroid receptors), gene activators (e.g. ICP4 in HSV-1, homeodomain proteins, NFκB, steroid receptors), and RNA polymerases (e.g., T7 phage RNA polymerase, T4 phage RNA polymerase, *Escherichia coli* RNA polymerase holoenzyme, eukaryotic RNA polymerases I, II and III). Sequence-specific DNA-binding proteins that function in DNA replication are known in the art, and are exemplified by the origin binding proteins that bind specifically to the origin of DNA replication in HSV-1 (ICP8), or *Escherichia coli* (DnaA)

Sequence-specific DNA-binding proteins that are involved in DNA recombination include, but are not limited to, those proteins that function in λ bacteriophage DNA integration into *Escherichia coli* DNA (λ integrase complex), in transposon recombination with host DNA (e.g. γ/δ resolvase), and in the recombination of genes responsible for generating the huge diversity of antibodies and T-cell receptors (Rag1/Rag2 proteins).

Sequence-specific DNA-binding proteins that function in DNA repair recognize and bind to nucleotide sequences containing one or more modifications. A "modification" as used herein in reference to a nucleic acid sequence refers to any change in the structure of the nucleic acid sequence. Changes in the structure of a nucleic acid sequence include changes in the covalent and non-covalent bonds in the nucleic acid sequence. Illustrative of these changes are point mutations, mismatches, strand breaks, as well as covalent and non-covalent interactions between a nucleic acid sequence, that contains unmodified and/or modified nucleic acids, and other molecules. Illustrative of a covalent interaction between a nucleic acid sequence and another molecule are changes to a nucleotide base (e.g., formation of thymine glycol) and covalent cross-links between double-stranded DNA sequences that are introduced by ultraviolet radiation or by cis-platinum. Yet another example of a covalent interaction between a nucleic acid sequence and another molecule includes covalent binding of two nucleic acid sequences to psoralen following ultraviolet irradiation. Non-covalent interactions between a nucleic acid sequence and another molecule include non-covalent interactions of a nucleic acid sequence with a molecule other than a nucleic acid sequence and other than a polypeptide sequence. Non-covalent interactions between a nucleic acid sequence with a molecule other than a nucleic acid sequence and other than a polypeptide sequence are illustrated by non-covalent intercalation of ethidium bromide or of psoralen between the two strands of a double-stranded deoxyribonucleic acid sequence.

For example DNA photolyase in *Escherichia coli* recognizes thymine dimers produced by UV irradiation; Ada protein recognizes methylated guanine and thymine in DNA, methylated Ada protein binds to a specific DNA sequence (Table 1, supra) and activates the transcription of genes involved in repair.

Sequence-specific DNA-binding proteins are commercially available (e.g., TBP in Example 2) and may also be made using methods known in the art, such using expression plasmids that encode these proteins (e.g., NFκB of Example 1, and λ cI repressor of Example 3).

2. Cognate nucleotide recognition sequences

The cognate nucleotide recognition sequences for a multitude of sequence-specific DNA-binding molecules are known in the art (exemplified in Table 1, supra). Additionally, the cognate nucleotide recognition sequence for any sequence-specific DNA-binding molecule may readily be determined using methods that are well known in the art such as in vitro DNA footprinting [Lakin (1993) In: "Transcription Factors. A Practical Approach" Latchman, D. S. editor, pp. 27–47. IRL Press, New York] and gel retardation assays [Dent, C. L., and Latchman, D. S. (1993) The DNA mobility shift assay. In: "Transcription Factors. A Practical Approach" Latchman, D. S. editor, pp. 1–26. IRL Press, New York].

3. Detecting the presence, and determining the activity, of sequence-specific DNA-binding molecules The present invention further provides methods for detecting the presence, and determining the DNA-binding activity of a sequence-specific DNA-binding molecule. The methods provided herein exploit the principle, that was discovered by the inventors, that when a sequence-specific DNA-binding molecule binds to its cognate nucleotide recognition sequence contained in a plasmid that also contains a unique restriction site (i.e., a restriction site that is located either within or substantially adjacently to the cognate nucleotide recognition sequence but not contained elsewhere on the plasmid), such binding protects the unique restriction site from cleavage (i.e., reduces cleavage) by a restriction enzyme that would otherwise be capable of cleaving at this restriction site in the absence of binding of the sequence-specific DNA-binding molecule to its cognate nucleotide recognition sequence. This method has the advantage of providing a specific and sensitive assay for the detection and quantitation of the DNA-binding activity of sequence-specific DNA-binding molecules. The method is schematically depicted in FIG. 1.

Cleavage of a plasmid may be determined by a number of methods known in the art. In a preferred embodiment, cleavage of the plasmid is determined using agents that intercalate double stranded DNA and result in fluorescence. For example, cleavage of the plasmid by a restriction enzyme is determined by observing a reduction in the level of fluorescence in a sample containing the plasmid and restriction enzyme as compared to the level of fluorescence in a sample that contains the plasmid in the absence of the restriction enzyme.

The specificity of the methods provided herein is determined by the nucleotide sequence of the cognate nucleotide recognition sequence in the plasmids of the invention. The cognate nucleotide recognition sequence may be experimentally modified to achieve greater affinity of binding to the sequence-specific DNA-binding molecule, thus increasing the specificity of the invention's methods.

The sensitivity of the invention's methods is determined by several factors including the binding affinity of the sequence-specific DNA-binding molecule to its cognate nucleotide recognition sequence, plasmid size, the type of reagent that intercalates double stranded DNA, and fluorometer design. With respect to the binding affinity of the sequence-specific DNA-binding molecule to its cognate nucleotide recognition sequence, greater sensitivity is obtained when using molecules that bind with a relatively higher affinity to their cognate nucleotide recognition sequence than when using molecules that bind with a relatively lower affinity to their cognate nucleotide recognition sequence, since the former molecules "protect" the restriction site at relatively lower concentrations than the latter molecules.

With respect to the size of the plasmid, binding of a sequence-specific DNA-binding molecule to its cognate nucleotide recognition sequence that is located in a first plasmid that is larger than a second plasmid containing the cognate nucleotide recognition sequence results in greater sensitivity of detection and/or quantitation since a single cleavage event causes the linearization of a relatively larger amount of DNA. The resulting drop in fluorescence per cleaved plasmid molecule increases with the size of the plasmid.

With respect to the type of reagent that intercalates double stranded DNA, a number of commercially available intercalating dyes are available. Some intercalating dyes (e.g., bis-ethidium, PICOGREEN®, POPO, TOTO) result in greater fluorescence than ethidium bromide when intercalating into the same amount of double-stranded DNA. Since these dyes thus allow detection of a smaller number of plasmid molecules compared to the number of plasmid molecules detected with ethidium bromide, these dyes offer greater sensitivity than ethidium bromide.

With respect to the fluorometer design, the sensitivity of the fluorometer can be increased by decreasing the volume of the cuvette or by using microtiter plates. One of skill in the art appreciates that laser fluorometers, photomultiplier detectors and other design improvements can further increase sensitivity.

In conducting an assay for determining the DNA-binding activity of a sequence-specific DNA-binding molecule, the following samples are preferably, though not necessarily, included (1) a blank sample containing a plasmid of the invention (e.g., a plasmid that contains a restriction enzyme binding sequence, a unique restriction site, and the cognate nucleotide recognition sequence for the molecule whose DNA-binding activity is to be determined), (2) a control sample containing the same amount of the plasmid as in the blank sample and additionally containing an amount of a restriction enzyme capable of cleaving at the unique restriction site, (3) a set of standard samples containing the same amount of the plasmid as in the blank and control samples, the same amount of restriction enzyme as in the control sample, and additionally containing known and different amounts of the sequence-specific DNA-binding molecule, and (4) one or more test samples containing the sample to be tested for the activity of the sequence-specific DNA-binding molecule, and containing the same amount of the plasmid and the restriction enzyme as in the control sample. To detect the presence of (rather than to quantitate) a sequence-specific DNA-binding molecule, standard samples need not be included.

The above-listed samples are prepared using the following steps. First, the plasmid carrying the cognate nucleotide recognition sequence and unique restriction site is incubated with a sample containing the sequence-specific DNA-binding molecule under conditions that allow binding of the molecule to its cognate nucleotide recognition sequence. Such conditions are known in the art for a plethora of sequence-specific DNA-binding molecules (examples are shown in Table 1). The binding conditions of sequence-specific DNA-binding molecules to their cognate nucleotide recognition sequences refer to temperature, pH, salt concentrations (e.g. concentration of $Na^+$, $Mg^{++}$, $Ca^{++}$, and other ionic species), and requirements for cofactors (e.g. hormones, trace metal ions, other proteins). These condition are known in the art since they are usually determined at the time of discovery of a sequence-specific DNA-binding molecule, when binding is detected by gel electrophoresis techniques, such as footprinting [Lakin (1993) supra] and gel retardation assays [Dent, C. L. and Latchman, D. S., 1993, supra]. Those conditions can be applied directly to the assay described in this invention or they can be modified, if desired, e.g., to allow restriction of the plasmid in the control sample by the restriction enzyme therein. Conditions for binding the sequence-specific DNA-binding molecule to its cognate nucleotide recognition sequence that are suitable for the assays of this invention can be readily determined using different concentrations of ions, detergents, hormones or other reagents, until the maximum protection (e.g., as detected by the maximum reduction in the amount of uncleaved plasmids of the invention in the standard samples compared to the amount of uncleaved plasmid in the control sample) of the restriction site by the bound sequence-specific DNA-binding molecule is achieved.

Second, a restriction enzyme that is capable of cleaving at the unique restriction site is added to the above mixture of plasmid and sequence-specific DNA-binding molecule at a suitable concentration and for a suitable period of time. Preferably, the concentration of the restriction enzyme and the time of incubation are selected to obtain a defined mathematical (e.g., linear, exponential, hyperbolic, etc.) relationship between the amount of sequence-specific DNA-binding molecule present in the standard samples and the amount of double-stranded DNA present after digestion with the restriction enzyme in the samples (e.g., FIGS. 6, 9, 10 and 12).

Two approaches may be adopted to determine the suitable amount of restriction enzyme and suitable incubation period. The selection of the approach depends on the binding kinetics of the sequence-specific DNA-binding molecule to its cognate nucleotide recognition sequence. Type I binding kinetics represent "stoichiometric" binding between the sequence-specific DNA-binding molecule and its cognate nucleotide recognition sequence. Stoichiometric binding occurs when sequence-specific binding protein binds relatively rapidly (e.g., with a $K_{on}$ of about $10^6$ $M^{-1}$ $sec^{-1}$ or greater) to its cognate nucleotide recognition sequence, and it dissociates relatively slowly (e.g., with $K_{off}$ of 0.05 $sec^{-1}$ or less) such that once bound, the molecule does not dissociate from its cognate nucleotide recognition sequence at a significant rate during the time of the assay. Thus, when the restriction enzyme is added, it preferably will cut only those plasmids that have the restriction enzyme cleavage site unprotected by the sequence-specific DNA-binding molecule. The amount of restriction enzyme added should be sufficiently high, and the time of incubation should be sufficiently long, to allow cleavage (preferably to completion) of the unbound DNA as detected by, for example, a reduction of fluorescence units following heat denaturation and incubation with an agent (e.g., ethidium bromide) that intercalates between the base pairs of dsDNA. Therefore, the extent of binding of the sequence-specific DNA-binding molecule to its cognate nucleotide recognition sequence is measured as the amount of fluorescence detected after incubation with the restriction enzyme. Type I binding kinetics are exemplified herein by the binding kinetics of the TATA box binding molecule (TBP), the λ cI repressor, and RNA polymerase to their cognate nucleotide recognition sequences described in Examples 2 to 4, infra.

Type II binding kinetics represent "competitive" binding between the sequence-specific DNA-binding molecule to its cognate nucleotide recognition sequence on the one hand, and between the restriction enzyme to its cognate nucleotide recognition sequences on the other hand. Competitive binding occurs where the sequence-specific DNA-binding molecule has relatively high $k_{off}$ (ie., more than 0.05 sec$^{-1}$), and where the number of sequence-specific DNA-binding molecules bound to their cognate nucleotide recognition sequence at a given time is the result of the equilibrium between $k_{off}$ and $k_{on}$. This means that the sequence-specific DNA-binding molecule will compete with the restriction enzyme for the unique restriction sites. The binding of the sequence-specific DNA-binding molecule to its cognate nucleotide recognition sequence does not result in permanent protection of the restriction site, but rather in a reduction in the rate of cutting by the restriction enzyme. Thus, the amount of binding of the sequence-specific DNA-binding molecule to its cognate nucleotide recognition sequence is measured by the reduction of the rate of cutting by the restriction enzyme. Therefore, in Type II binding kinetics, the amount of restriction enzyme and the length of time of incubation are more important for the proper quantitation of a DNA-binding activity than they are in Type I binding kinetics. The amount of cccDNA remaining should be measured after a fixed period of time that is chosen so that the amount of dsDNA remaining is proportional to the amount of sequence-specific DNA-binding molecule added to the reaction, according to a defined mathematical (e.g., linear, exponential, hyperbolic, etc.) function. This time period may be determined by performing a time course of digestion of the plasmid with the restriction enzyme, in the presence and in the absence of the sequence-specific DNA-binding molecule (see, e.g., FIG. 5). In the illustrative Example 1, the time of 5 minutes was chosen because the time kinetics of cutting approached a straight line during the first 5 minutes, both in the absence and in the presence of the sequence-specific DNA-binding molecule, the molecule NFκB. Type II binding kinetics are herein illustrated by the binding kinetics of NFκB to its respective cognate nucleotide recognition sequences described in Example 1, infra.

In the third step of conducting the assay, restriction digestion reaction is stopped after the desired time (usually, though not necessarily, from 5 to 20 min) by, for example, transferring the sample to a pH 12 buffer (e.g., for ethidium bromide fluorometry as described in the Experimental section below), or by adding sodium EDTA or other chemicals that chelate Mg$^{++}$ ions thereby inhibiting the restriction enzyme activity.

Figure 2:
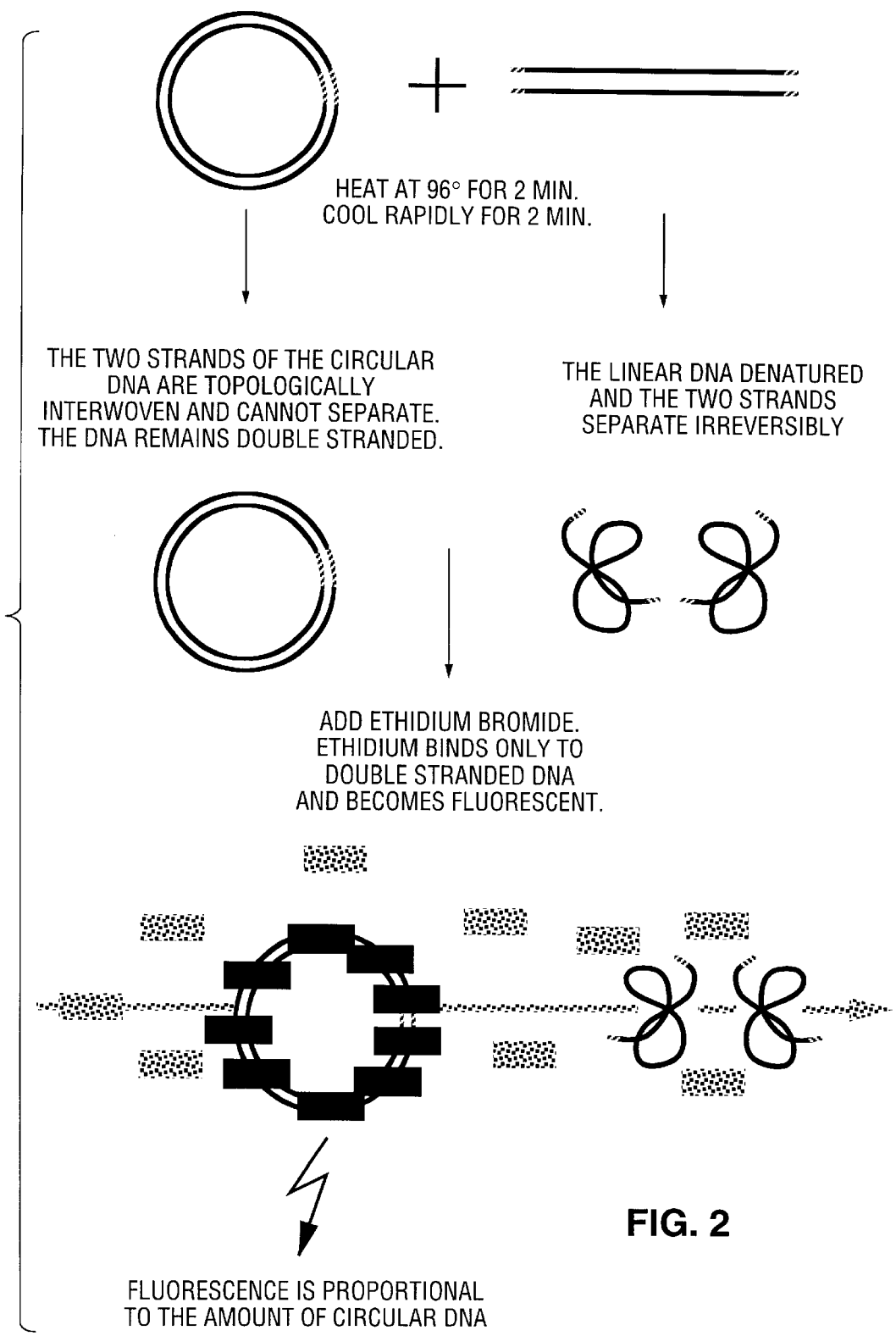
FIG. 2 is a schematic representation of the exemplary fluorescence method used for detecting and quantitating the presence of uncleaved plasmid DNA.

Finally, the amount of plasmid that was not cleaved by the restriction enzyme is measured using any one of several methods known in the art, e.g. fluorescence using ethidium bromide or other commercially available dyes that intercalate dsDNA, gel electrophoresis followed by densitometry of the cccDNA band, or gel electrophoresis followed by hybridization with a radioactive probe that is specific for the uncleaved sequence that spans the restriction site. In a preferred embodiment, the amount of remaining dsDNA is measured using the fluorometry method previously described [Morgan et al. (1979) Nucl. Acid Res. 7:547–569; Morgan et al. (1979) Nucl. Acids Res. 7:571–594] and summarized in FIG. 2. Briefly, the plasmid is heated at 96° C. (2 min) and cooled rapidly (2 min) to room temperature. At 96° C., if the DNA has been cleaved, the DNA is denatured, the two strands separate and cannot renature during the time of the assay (approximately 20–60 min). In contrast, in the DNA that has not been cleaved, the two strands are topologically linked and cannot diffuse away from each other, so that they will immediately renature upon cooling to room temperature. The amount of dsDNA (i.e., uncleaved plasmid) can be readily measured by adding a dye that intercalates between base pairs of double stranded DNA and that produces a fluorescence that is proportional to the amount of the intercalating dye bound to the plasmid. Examples of such commercially available dyes include bis-ethidium bromide, "PICOGREEN," "TOTO," "POPO" (Molecular Probes Inc., Eugene, Oreg.) or others that can be used following the manufacturer's conditions of pH and concentration [Haugland (1992) Handbook of fluorescent probes and research chemicals. Molecular Probes, Inc.]. In a preferred embodiment, 0.5 µg/ml of ethidium bromide (Sigma Chemical Co., St. Louis, Mo.) is used at pH 12 as previously described [Morgan et al. (1979) Nucleic Acid Res. 7:547–569; Morgan et al. (1979) Nucleic Acid Res. 7:571–594].

To detect the presence of the sequence-specific DNA-binding molecule, the amount of uncleaved plasmid in a control sample (that was incubated in the absence of the sequence-specific DNA-binding molecule) is compared to the amount of uncleaved plasmid in the test sample. The detection of a greater amount of uncleaved plasmid in the test sample as compared to the amount of uncleaved plasmid in the control sample indicates the presence of the sequence-specific DNA-binding molecule in the test sample.

The amount and/or concentration of DNA-binding activity (Q) in a test sample may be calculated as follows:

$$Q = \frac{A-B}{C-B} \times E$$

where A is the number of fluorescence units in the test sample; B is the number of fluorescence units in the control sample, C is the number of fluorescence units in a standard sample, and E is the amount and/or concentration (respectively) of DNA-binding molecules in the standard sample.

C. Methods for determining the initiation of transcription activity of RNA polymerases The invention provides methods for detecting, as well as determining, the activity of RNA polymerases in initiating transcription of a DNA sequence into an RNA sequence. The methods of the invention may readily be carried out, using the teachings herein, in most laboratories and also offer the advantages of rapidity, ease of automation to increase throughput (e.g., for screening of drugs directed against RNA polymerase), and not requiring the use of radioactivity. This section is further described under (1) RNA polymerases, and (2) detecting and determining the initiation of transcription activity of RNA polymerases.

1. RNA polymerases

RNA polymerases constitute a family of enzymes that transcribe DNA sequences into complementary RNA molecules. Transcription is a fundamental process of life that is required to use the information contained in the DNA in order to produce all of the proteins that are needed for the proper functioning of a cell. The first step of transcription is the binding of the RNA polymerase complex to its cognate DNA recognition sequence, that is usually contained in the promoter. This binding requires the presence of various co-factors, most of that are sequence-specific DNA-binding proteins themselves. Following the binding of all the required factors and the presence of ribonucleotide triphosphates (rNTPs), the RNA polymerase leaves its cognate DNA recognition sequence, and moves along the DNA template to synthesize an RNA molecule (the transcript).

RNA polymerases are present in all cells (prokaryotes, eukaryotes, Archaea and in some viruses) and their activity is essential for the production of all molecules in the cell. Table 1 supra, provides examples of RNA polymerases, their sources and cognate nucleotide recognition sequences.

RNA polymerases may be composed of a single polypeptide sequence (e.g., RNA polymerases from the bacteriophages T7 and T3, and mitochondrial RNA polymerase) that binds to its cognate nucleotide recognition sequence without the need for any other cofactor.

In contrast to viral RNA polymerases, bacterial RNA polymerases are composed of 5 subunits, $\alpha1, \alpha2, \beta1, \beta2$ and $\sigma$ and the $\sigma$ subunit is the major determinant of binding specificity. Other factors may be required for binding of the RNA polymerase to its cognate nucleotide recognition sequence and for initiation of transcription from certain promoters.

Eukaryotic cells have 3 known types of RNA polymerases: Polymerase I, that transcribes ribosomal RNAs, Polymerase II, that transcribes most of the protein-encoding genes, and Polymerase III, that transcribes tRNAs and 5S ribosomal RNA, and sn RNAs. Each of these polymerases is composed of a number of subunits, and binds to different promoters, forming an "initiation complex" with a variety of other initiation factors (e.g., TBP, TFIIA, TFIIB). The binding specificity and strength of binding of the RNA polymerase is determined by the initiation factors of the "initiation complex" (i.e., a complex of RNA polymerase and initiation factors). Some of these initiation factors are required for binding of the RNA polymerase to its cognate nucleotide recognition sequence and they are a necessary component of any initiation complex. The specificity of binding of the RNA polymerase to the promoter is determined by these initiation factors and not by the properties of the RNA polymerase per se. Transcription factors, that are different from the initiation factors, modulate the transcriptional activity of the RNA polymerase (i.e., its ability to start moving along the DNA to synthesize an RNA molecule as demonstrated by, for example, the rate of RNA synthesis) either by permitting, inhibiting or increasing the rate of transcription. Transcription factors usually bind specifically to the DNA template near the promoter region of specific genes.

RNA polymerases found in Archaea are less well characterized, but they have a complexity similar to eukaryotic RNA polymerases and they function in a manner similar to eukaryotic RNA polymerases by binding specifically to cognate nucleotide recognition sequences on the DNA template.

RNA polymerases are commercially available (e.g., T3 RNA polymerase, T7 RNA polymerase, and *Escherichia coli* RNA polymerase) (Amersham Pharmacia Biotech, Uppsala, Sweden), and may also be isolated using methods known in the art [Dignam et al. (1983) Nucleic Acid Res. 11:1475–1489].

Figure 3:
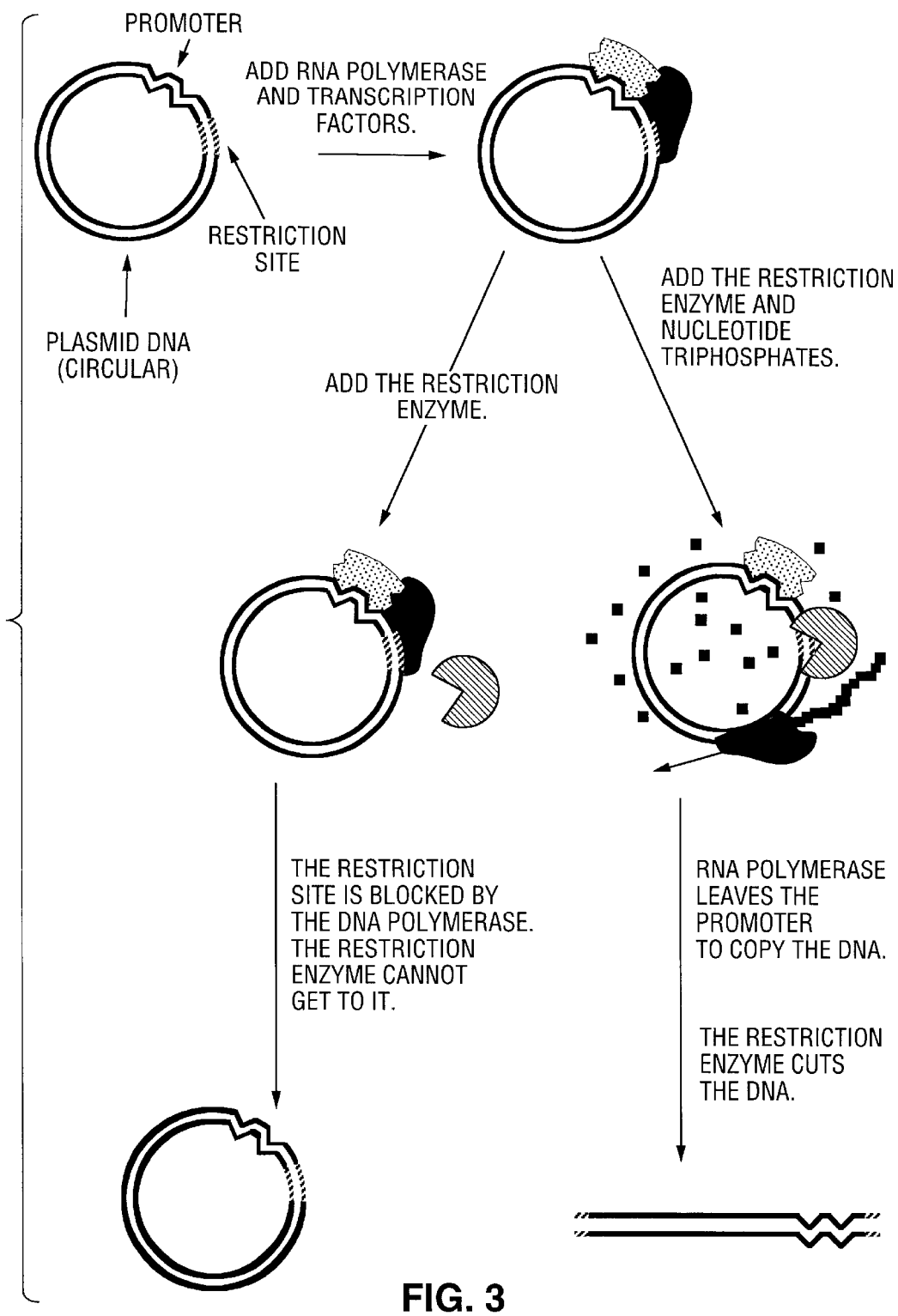
FIG. 3 is a schematic representation of an exemplary method for determining the initiation transcription activity of RNA polymerases.

2. Detecting and determining the initiation of transcription activity of RNA polymerases The invention provides methods for detecting, as well as determining, the activity of RNA polymerases in initiating transcription of a DNA sequence into an RNA sequence. The invention's methods are illustrated in FIG. 3 and are based on essentially the same principles as the methods for detecting and determining the activity of sequence-specific DNA-binding molecules as discussed supra. Briefly, a plasmid is constructed containing a cognate nucleotide recognition sequence (usually contained in a promoter sequence) for the RNA polymerase and a unique restriction site placed within or substantially adjacent to the RNA polymerase's cognate nucleotide recognition sequence. An amount of RNA polymerase that is sufficient to saturate all its cognate nucleotide recognition sequences is added. The amount of RNA polymerase may be experimentally determined for each RNA polymerase using methods known in the art. Without intending to limit the invention to any particular mechanism, it is the inventors' view that when the RNA polymerase binds to its cognate nucleotide recognition sequence, the restriction site is protected from cleavage by the restriction enzyme. After binding of the RNA polymerase to its cognate nucleotide recognition sequence, the restriction enzyme is added and cleavage of the double stranded plasmid is measured as described above.

In order to measure initiation of transcription, a sufficient amount (e.g., 50 to 1000 $\mu$M) of each of the ribonucleotide triphosphates ATP, CTP, GTP and UTP is added to the reaction and cleavage of the plasmid is measured again after a desired time period. This time period is selected such that the restriction enzyme cleaves (preferably to completion) the plasmid in the absence of RNA polymerase. In the presence of RNA polymerase that has initiation of transcription activity, the RNA polymerase leaves the promoter and moves along the DNA, as it synthesizes an RNA molecule. As a result, the unique restriction site becomes accessible to the restriction enzyme and the plasmid is cleaved (FIG. 3). The extent of cleavage of the plasmid (e.g., as measured by drop in fluorescence following addition of an agent that intercalates dsDNA and after heat denaturation) represents the number of molecules that have left the promoter during the duration of the assay.

In order to determine the effects (e.g., increase, decrease) of a compound (e.g., drug or a transcription factor) on the RNA polymerase initiation of transcription activity, the extent of cleavage of the plasmid is measured using, preferably, (a) a positive control sample containing RNA polymerase and ribonucleotide triphosphates, in the absence of the test compound, (b) a negative control sample containing RNA polymerase in the absence of both ribonucleotide triphosphates and the test compound, and (c) a series of test samples containing RNA polymerase, ribonucleotide triphosphates and increasing amounts of the test compound. The amount of cleaved plasmid is determined as described above (e.g., using fluorescence).

The relative effect of the test compound on RNA polymerase initiation of transcription activity can be determined using the following equation:

$$R = \frac{A - B}{A - C}$$

Where A is the number of fluorescence units (proportional to the amount of uncleaved plasmid) in the negative control sample, B is the number of fluorescence units in the test samples, and C is the number of fluorescence units in the positive control sample. Inhibitors of RNA polymerase initiation of transcription will produce a R value of less than 1, while activators of RNA polymerase initiation of transcription will produce a R value greater than 1.

Because of the fundamental role of RNA polymerases in life processes, RNA polymerases are excellent targets for drugs aimed at killing undesirable cells, e.g., antibiotics (e.g., rifampicin) and anti-cancer drugs (e.g, α-amanitin) that inhibit transcription in bacteria and eukaryotic cells, respectively. The methods provided herein are thus useful in determining the activity of candidate therapeutic agents that are aimed at inhibiting initiation of transcription by RNA polymerases.

The methods of the invention are also useful in detecting and determining the regulatory activity of sequence-specific DNA-binding molecules that play a role in modulating RNA polymerase initiation of transcription activity. These methods offer the advantage over the invention's above-described methods for detecting and determining the DNA-binding activity of increased accuracy in those cases in that the activity of a sequence-specific DNA-binding molecule in modulating RNA polymerase initiation of transcription activity is modified by ligands (e.g.,drugs, hormones, other molecules) while the activity of the molecule in binding to DNA is not affected by these ligands. For example, the mercury binding protein (MerR) in bacteria binds to a specific sequence on the DNA and inhibits the transcript of several genes involved in mercury de-toxification; however, however, when mercury binds to the mercury-binding molecule, stimulation of the RNA polymerase is achieved. Some mutated forms of the estrogen receptor found in breast cancers can still bind to their cognate nucleotide sequence on the DNA, but they have lost their ability to activate transcription; as a result, breast cancers with such types of estrogen receptor are unresponsive to anti-estrogenic therapy.

Moreover, the methods of this invention can be used for screening and characterization of molecules that target and modify the activity of sequence-specific DNA-binding molecules in modulating RNA polymerase initiation of transcription activity The methods of the present invention further find use in detecting the presence and amount of environmental contaminants. For example, the plasmids of the invention may be engineered to contain the cognate nucleotide recognition sequence for a bacterial mercury suppressor protein. The mercury suppressor protein (MerA) binds to its cognate DNA sequence and inhibits transcription in the absence of mercury. In the presence of nano-molar concentrations of mercury, MerA becomes a transcription activator. Thus, the level of mercury in a sample may be determined by using the sample in the methods provided herein, whereby the measurement of RNA polymerase transcriptional activity will depend on the presence or absence of mercury.

EXPERIMENTAL

The following examples serve to illustrate certain preferred embodiments and aspects of the present invention and are not to be construed as limiting the scope thereof.

EXAMPLE 1
Determining sequence-specific DNA-binding activity of NF-κB using plasmid pDNAB-NFκB The following experiments were designed to determine the sequence-specific DNA-binding activity of NF-κB to a cognate nucleotide recognition sequence genetically engineered into a plasmid. NF-κB is a transcription factor homologous to the product of the oncogene v-rel and related proteins. NF-κB is a candidate target for anticancer therapy and for chronic inflammatory diseases, such as rheumatoid arthritis. Drugs that are able to prevent its activation or that inhibit its DNA binding affinity, would greatly potentiate the action of existing anticancer drugs.

The fully functional NF-κB factor is normally composed of 2 homologous subunits, p50 and p65, that form a heterodimer through homologous isomerization motifs. Two subunits of p50 can also form a dimer and can bind to a specific sequence of DNA. In vitro, the p50 subunits show specific DNA-binding activity. The three-dimensional structure of the p50 subunit bound to DNA has been solved by X-ray crystallography.

NFκB is found in the cytoplasm of mammalian cells bound to members of a family of proteins that inactivate the NFκB by blocking its DNA-binding domain and preventing its translocation to the cell nucleus. These inhibitors include proteins of the IκB family (IκB α, β and γ) and the precursors of the p50 molecule, NFκB1 (p105) and NFκB2 (p100). NFκB is activated by proteolytic removal of the inhibitor protein, probably mediated by ubiquitinylation and the proteasome complex.

Activation of NFκB can be stimulated by a number of extracellular agents, such as phorbol myristyl acetate (PMA), lipopolysaccharide (LPS), tumor necrosis factor (TNF), for that NFκB acts as an effector in a variety of tissues. The primary signal at the cell surface results in the binding of NFκB to its specific promoters on DNA in the nucleus and in the activation of genes involved in the regulation of cell proliferation, inflammation, HIV activation, and other processes. There is strong evidence suggesting that activation of NFκB results in the inhibition of programmed cell death (apoptosis) during development. Following the action of cytotoxic stimuli (e.g., TNF, ionizing radiation or anticancer drugs), NFκB is activated and cell death is reduced. Furthermore, the action of anticancer agents is potentiated by drugs that prevent NFκB activation, such as the glucocorticoids, that induce the synthesis of IκB, or aspirin and inhibitors of proteasomes, that prevent IκB degradation.

A. Construction of plasmid pDNAB-NFκB and production of NFκB p50 protein

The plasmid (pDNAB-NFκB) having the NFκB nucleotide recognition sequence was constructed using standard cloning techniques as follows. A synthetic oligonucleotide having the sequence 5'-GATCGAGGAGGGAAATTCCTGCA-3' (SEQ ID NO:63) (FIG. 4a) was inserted between the BamHI and PstI sites of the vector pUC19 (pUC19 is available from a variety of sources, e.g. Life Technologies Inc., Gaithersburg, Md., GenBank Accession #L09137). It was not necessary to synthesize the complementary oligonucleotide, since the oligonucleotide was ligated between the 3'-recessed end produced by BamHII and the 5'-recessed end produced by PstI. The resulting product, a partially single-stranded circular plasmid, was transfected into the *Escherichia coli* host and cloned. The sequence of the cloned oligonucleotide was verified by sequencing. The synthesized oligonucleotide contains a BseRI binding sequence (5'-GAGGAG-3') situated upstream (with bine nucleotide overlap) to the NFκB nucleotide recognition sequence of the interferon β gene. The site of cutting by BseRI falls within the NFκB nucleotide recognition sequence.

The NFκB p50 protein was expressed using a plasmid containing the cDNA sequence coding for the amino acids 1 to 365 of the p50 protein (GenBank accession #25 16335504) as previously described [Muller et al. (1995) Nature 373:311–317]. This polypeptide fragment contains the DNA-binding domain, and has been used to solve the structure of the NFκB p50 protein bound to DNA . Plasmid pNFκB was cloned in *Escherichia coli* strain "SURE" (Stratagene, La Jolla, Calif.) and the expression of the p50 protein was induced by 0.1 mM IPTG for 3 hours. The cells were pelleted, resuspended in buffer A (20 mM HEPES [pH 7.5], 1 mM DTT, 2 mM EDTA, 0.4 M NaCl, 0.5 mM PMSF, 5% glycerol, 1 μg/mL pepstatin A, 1 μg/mL leupeptin) and disrupted by sonication. The debris was pelleted at 30,000×g for 30 min and the supernatant was incubated with 3.75% polyethyleneimine to precipitate insoluble material. After spinning at 20,000×g for 25 min the supernatant was fractionated by addition of ammonium sulfate to a final of 55% saturation. After spinning at 30,000×g for 20 min the pellet was resuspended in buffer A without NaCl. The NFκB was purified on a SP-Sepharose column (Pharmacia, Uppsala, Sweden) by elution with a linear gradient of NaCl from 0 to 0.5 M NaCl. Fractions that had peak protein content were analyzed by 10% PAGE gel electrophoresis. Fractions containing NFκB were pooled and stored in 20% glycerol at −20° C., where NFκB DNA-binding activity in the purified extract was maintained for at least 6 months.

B. Time course for restriction by BseRl in the presence or absence of NFκB

Binding of NFκB to the pDNAB-NFκB plasmid was performed in a buffer containing 10 mM TRIS (pH 7.5) 50 mM NaCl, 1 mM DTT and 10 mM MgCl$_2$. The mixture contained 0.12 μg/μL of DNA and 6 ng/μL of NFκB, prepared as described above. Incubation was carried out at 25° C. for 5 min. After this incubation, 0.02 U/μL of BseRI restriction enzyme (New England Biolabs, Beverly, Mass.) were added to the mixture, and at appropriate times 10 μL of the mixture were transferred to a 1.2 mL of pH 12 fluorescence buffer (10 mM K$_2$PO$_3$, 1 mM EDTA, 0.5 μg/mL ethidium bromide). Ethidium bromide fluorescence was measured at 525 nm excitation, 605 nm emission, after heating for 2 minutes at 96° C. and cooling rapidly to room temperature. FIG. 5 shows the time course of the drop in level of fluorescence (i.e., the amount of cutting by the restriction enzymes) over the time of the experiment. These results show that the presence of NFκB decreases the rate of digestion by BseRl, but does not prevent it completely. This represents competitive protection, described above as Type II binding kinetics.

C. Quantitation of NFκB DNA-binding activity

Based on the time course of FIG. 5, the following conditions were selected to quantitate NFκB. Binding was allowed to proceed for 5 minutes in the presence of about 0.5 μg of DNA plasmid and NFκB extract, in a final volume of 20 μL. This was followed by the addition of 0.2 U of BseRI (New England Biolabs, Beverly, Md.) and incubation for 5 min at 25° C. The reaction was stopped by transferring the sample to the pH 12 fluorescence buffer.

FIG. 6 shows the results in fluorescence units (FU) following incubation of samples with different amounts of NFκB extract. Each point represents the average of 3 replicates and the error bars represent the standard deviation from the average. These results show that there is a linear relationship between the amount of NFκB added and the extent of protection of the plasmid from cleavage by BseRI, under the condition described supra. The data were fitted using a linear equation $$y = a + bx$$

where y is the fluorescence unit, a is the Y-axis intercept, b is the slope of the curve, x is the ng of proteins. These data gave the results of a=46.3 fluorescence units, b=20.6 fluorescence unit/ng of NFκB.

This standard curve can be used to calculate the amount (ng) and/or concentration (ng/μl) of active NFκB protein that specifically binds to its cognate DNA recognition sequence in a test sample using the formula $$x = \frac{y - a}{b}$$

This is equivalent to the above-described formula when using only one point as a standard sample. In fact b=(C−B) when NFκB is 1 ng (C is the number of fluorescence units in a standard sample, B is the number of fluorescence units in the control sample).

D. Specificity of NFκB binding to its cognate nucleotide recognition sequence

In order to show that inhibition of the restriction enzyme action was specific, NFκB extract was added to a sample prepared as described supra, containing either 0.5 μg of pDNAB-NFκB plasmid (that carried the NFκB cognate nucleotide recognition sequence) or 0.5 μg of pDNAB-TATA. The plasmid pDNAB-TATA is identical to pDNAB-NFκB except that it contains the cognate nucleotide recognition sequences for the TATA box binding protein (see FIG. 4b for the recognition sequence). Ethidium bromide fluorescence was measured as describe above and the percentage of uncut plasmid was determined by expressing the fluorescence of samples treated with restriction enzyme as a percentage of the fluorescence of control samples that were untreated with restriction enzyme and that contained 100% uncut plasmid.

Figure 7:
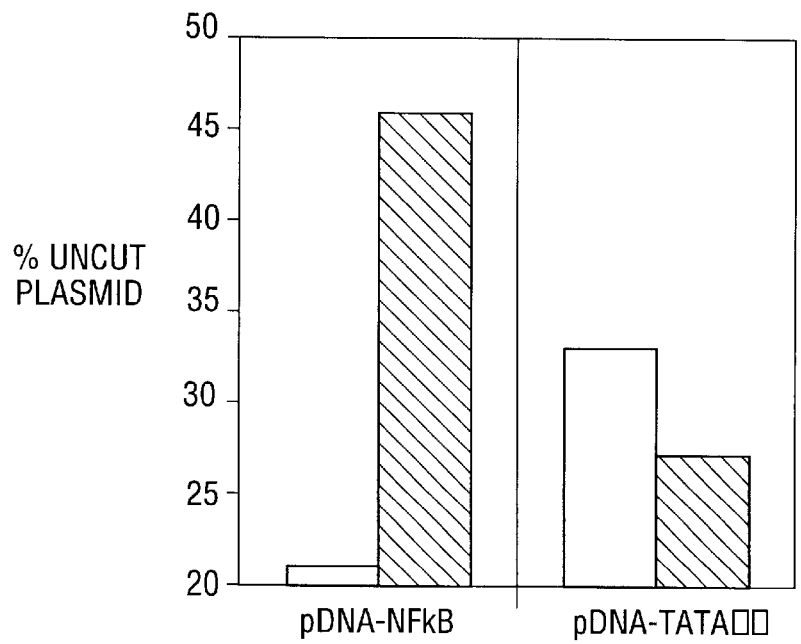
FIG. 7 is a bar graph showing the specificity of the NFκB assay for NFκB. Shaded and unshaded boxes are in the presence and absence, respectively, of NFκB.

The results are shown in FIG. 7. White bars represent control samples incubated in the absence of NFκB. Hatched bars represent samples containing NFκB protein. The samples were incubated for 5 min in the presence or absence of an excess of NFκK (200 ng/μL) and 0.02 U/μL of BseRI were added for 20 min, before measuring fluorescence. FIG. 7 shows that the presence of NFκB protects plasmid pDNAB-NFκB, but not plasmid pDNAB-TATA that does not carry a NFκB recognition sequence, from restriction by BseRI. The drop of fluorescence observed in the sample containing NFκB and pDNAB-TATA was due to non-specific endonuclease activity contaminating the NFκB preparation.

As shown in FIG. 7 the presence of NFκB protected only the plasmid carrying the NFκB cognate nucleotide recognition sequence, but had no effect on cleavage of the plasmid carrying the cognate nucleotide recognition sequence of another DNA-binding proteins. These results show the specificity of NFκB for its cognate nucleotide recognition sequence on plasmid pDNAB-NFκB.

EXAMPLE 2

Determining the sequence-specific DNA-binding activity of the TATA box binding protein (TBP) using plasmid pDNAB-TATA The experiments in this example were conducted to determine the DNA-binding activity of the TATA binding protein (TBP) to its cognate nucleotide recognition sequence. TBP is the first protein believed to be required in assembling the eukaryotic RNA polymerases on the promoter. It binds strongly to its cognate DNA recognition sequence (dissociation constant about $10^{-12}$M) and hence its activity can be measured by the inventions' fluorescence assay stoichiometrically, ie., all the available TBP binds the DNA and blocks cleavage at the BseRl restriction site.

A. Construction of plasmid pDNAB-TATA

The TBP cognate nucleotide recognition sequence (5'-TTTTATA-3') (FIG. 4B) was introduced into pUC19 by inserting the chemically synthesized nucleotide sequence 5'-GATCGAGGAGGGGTATAAAAGGCCTGCA-3' (SEQ ID NO:64) into the BamHI and PstI overhangs in pUC19 as described above (Example 1) for NFκB.

B. Measuring sequence-specific DNA-binding activity of TBP

The reaction with BseRI contained 10 mM Tris HCl (pH 8), 25 mM KCl, 2 mM spermidine, 0.1 mM EDTA, 0.025% NP40, 5% glycerol, 0.5 mM DTT, 0.1 mg/ml denatured gelatin, 5 mM MgCl$_2$. Human TBP (Promega, Madison, Wis.) was added and incubated at 22° C. for 40 minutes to allow complete binding. After this incubation, 1.6 U of BseRI were added in a final volume of 32 μL.

Figure 8:
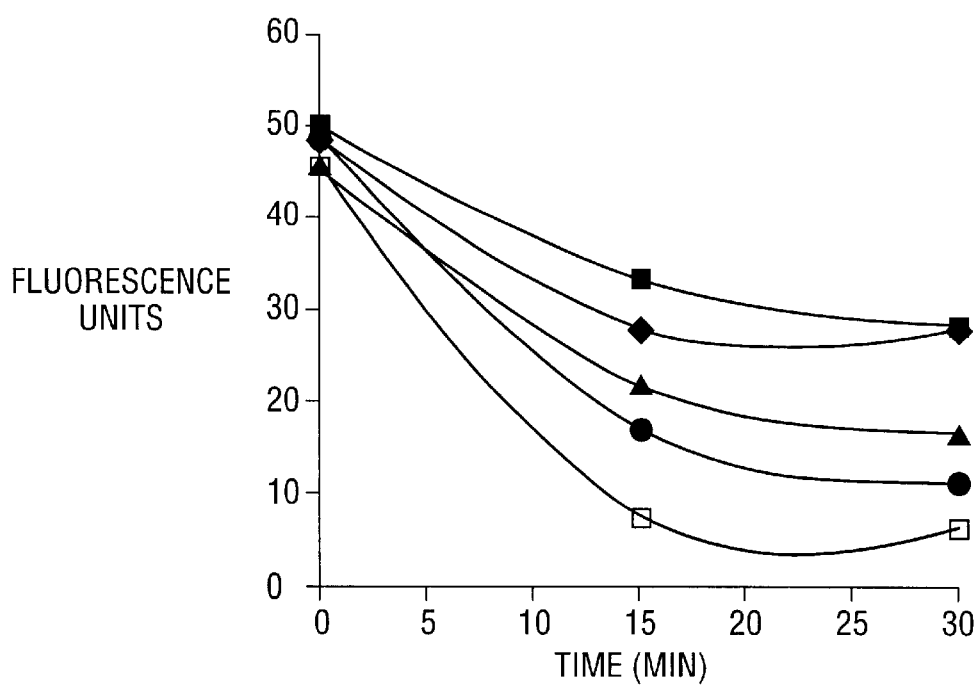
FIG. 8 is a graph showing a time course for protection of plasmid pDNAB-TATA by TBP from digestion by BseRI in the presence of 0 ng TBP (open square), 3.3 ng TBP (filled circle), 6.7 ng TBP (filled triangle), 13 ng TBP (filled diamond), and 20 ng TBP (filled square).

FIG. 8 shows the time course of BseRI digestion in the presence of increasing concentrations of TBP. TBP binds with Type I kinetics, and stoichiometrically prevents digestion by BseRI during the time of the assay, so that the extent of cutting by BseRI reaches a plateau that is maintained during the time of the experiment.

Figure 9:
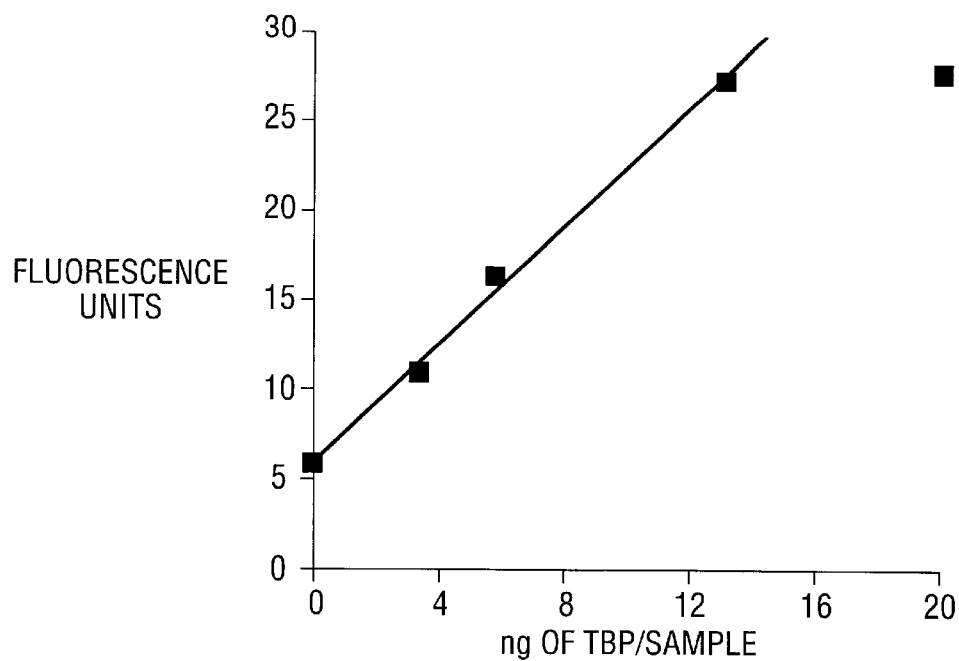
FIG. 9 is a graph showing quantitation of TBP DNA-binding activity.

To quantitate the amount and/or concentration of TBP in the tested samples, fluorescence values at 30 min were derived from FIG. 8 as shown in FIG. 9. FIG. 9 shows that the DNA-binding activity of TBP can be measured linearly over the concentration range of 4–15 ng.

EXAMPLE 3

Determining the sequence-specific DNA-binding activity of the bacteriophage λ cI repressor using plasmid pDNAB-or1

The experiments in this example were conducted to determine the DNA-binding activity of the bacteriophage-λ cI repressor to its cognate nucleotide recognition sequence.

The λ-phage cI repressor is the gene regulator needed to maintain the lysogenic status of a bacterium infected with the λ phage, i.e. the λ phage DNA remains integrated in the bacterial DNA and does not express the viral genes required for replication. The cI repressor acts by binding to specific operator sequences called OR1, OR2 and OR3, thereby preventing the transcription of the cro gene, the product of that activates the λ phage genes that are necessary for its lytic cycle.

A. Construction of plasmid pDNAB-or1

The ORI sequence (TATCACCGCCAGAGGTA) (SEQ ID NO:65) (FIG. 4c) was introduced into pUC19 by inserting the chemically synthesized nucleotide sequence 5'GATCGAGGAGATATCACCGCCAGAGG-TAAAATAGTTATCACCGCCAGAGGT ATGCA-3' (SEQ ID NO:66) into the BamHI and PstI overhangs in pUC19 as described above for NFκB (Example 1). This sequence also contains a unique EcoRV restriction site that overlaps with the lambda cI repressor cognate nucleotide recognition sequence.

B. Measuring Sequence-Specific DNA-binding activity of cI repressor

Wild-type cI repressor can be overexpressed in E. coli using one of the clones of the cI gene [e.g., plasmid pEA3000 described by Amman et al. (1983) Gene 25:167–178]. The cI protein can be purified from the bacteria using the column chromatographic methods described by Johnson et al. (1980) Methods Enxymol. 65:839–856, that yield a pure prepartion as judged by Coomassie blue staining of an SDS polyacrylamide gel electrophoresis. Samples were prepared by adding various amounts of purified cI repressor to 0.5 μg of plasmid pDNAB-or1 in EcoRV buffer (50 mM Tris-HCl, pH 8.0, 10 mM MgCl$_2$, 50 mM NaCl, 1 mM CaCl$_2$). The samples were then incubated at 25° C. for 20 minutes in order to allow the binding of cI repressor to its cognate nucleotide recognition sequence. 10 U of the restriction enzyme EcoRV were then added and the samples were incubated at 25° C. for 15 more minutes. This incubation time is sufficient to allow complete cleavage of unprotected pDNAB-cI plasmid by EcoRV. The amount of uncleaved plasmid was then measured as described above (Example 1).

Figure 10:
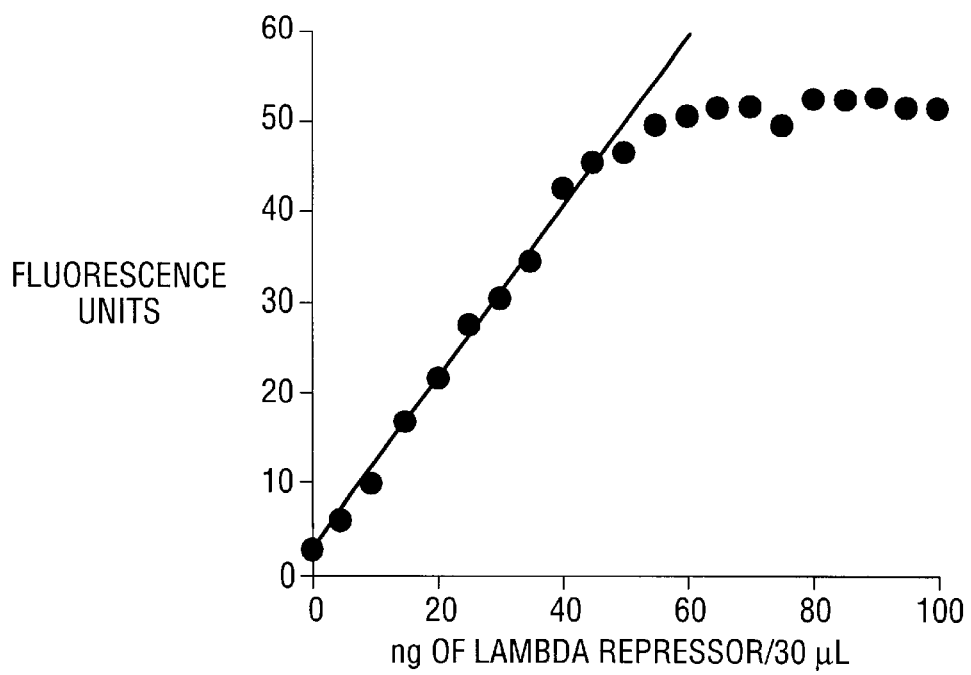
FIG. 10 is a graph showing quantitation of lambda-repressor DNA-binding activity.

FIG. 10 shows the results of this experiment. The protection of the plasmid from cleavage is directly proportional to the amount of cI repressor present in the sample, within a range of concentration between 5 and 60 ng of cI repressor. Above 60 ng the protection reaches a plateau because all available sites on the DNA are occupied by the lambda cI repressor molecule.

EXAMPLE 4

Determining the sequence-specific DNA-binding activity, and the initiation of transcription activity of RNA polymerase using plasmid pDNABtac The experiments in this example were conducted to measure both the binding activity of RNA polymerase to its cognate nucleotide recognition sequence, as well as the activity of RNA polymerase in initiating transcription. The activity of the inhibitor of transcription, rifampin, was measured.

A. Construction of plasmid pDNABtac

The synthetic oligonucleotide (5'-AGCTTGTTGACAATTAATCCTC CTCCTCGTATAATGTGTGGATGAC-3' (SEQ ID NO:67) with the consensus sequence (5'-TTG TCA-3') for the Escherichia coli RNA polymerase promoter (FIG. 4d) was cloned into pUC19 after removing a segment of the multiple-cloning site of pUC19 by Hind III and PstI cleavage to generate 5' HindIII and 3' PstI overhangs, respectively, using the same cloning strategy described above for NFκB (Example 1) to generate plasmid pDNAB-tac. pDNAB-tac contained two overlapping BseRI binding sequences and two restriction sites. The restriction sites were located within the RNA polymerase binding sequence.

B. RNA polymerase DNA-binding activity

The following experiment was conducted to measure the DNA-binding activity of RNA polymerase to its cognate nucleotide recognition sequence. The incubation buffer contained 50 mM tris HCl (pH 8), 5 mM MgCl$_2$, 100 mM potassium glutamate, and 3 μg of pDNABtac DNA in 60 μL final volume. One to 9 units of RNA polymerase (Boehringer-Mannheim, Mannheim, Germany) were added and, after preincubation at 37° C. for 5 minutes, the reaction was cooled to 31° C. (subsequent experiment showed that cooling at 31° C. was not necessary), 4 U of BseRI were added and incubated for varying time periods.

Figure 11:
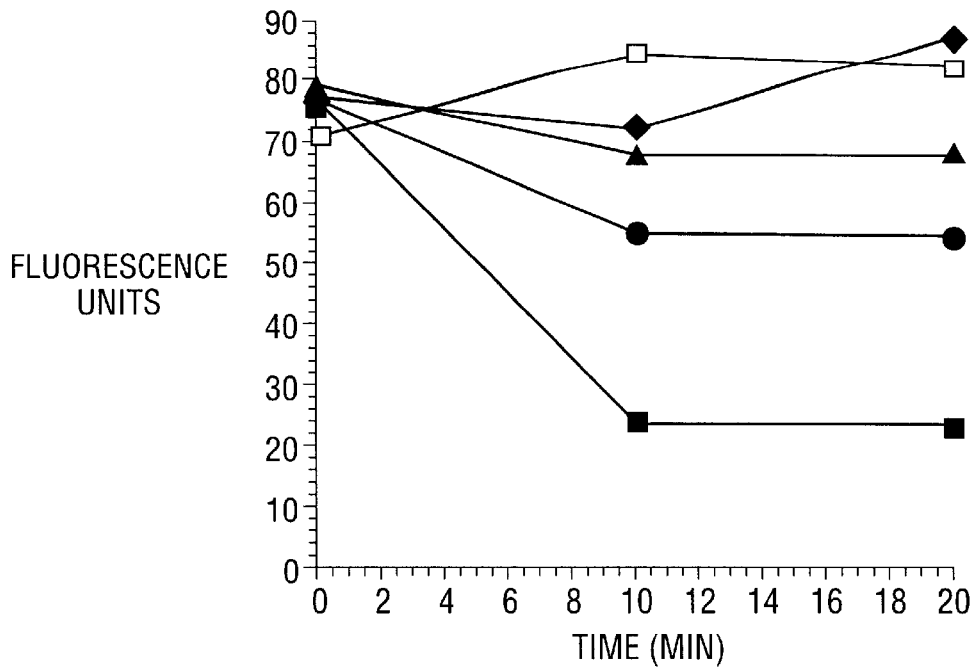
FIG. 11 is a graph showing a time course for protection of plasmid pDNAB-tac by *E. coli* RNA polymerase from digestion by BseRI in the presence of 1 Unit (filled squares), 3 Units (filled circles), 5 Units (filled triangles), 7 Units (filled diamonds) and 9 Units (open squares) of RNA polymerase.
Figure 12:
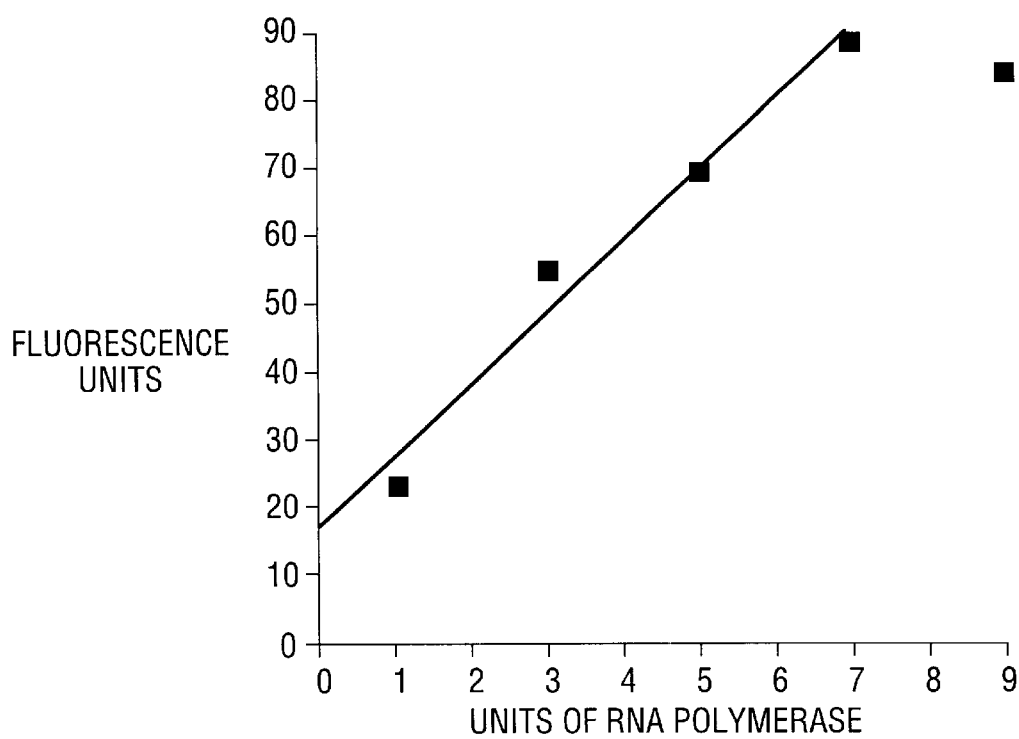
FIG. 12 is a graph showing the quantitation of the DNA-binding activity of *E. coli* RNA polymerase.

FIG. 11 shows the inhibition of BseRl cleavage over 20 min by increasing amounts of RNA polymerase. This inhibition represents stoichiometric inhibition of "Type I" as described above, ie., RNA polymerase reduced the fraction of plasmid that can be digested, rather than decreased the rate of cutting (as observed with NFκB, supra). This means that the time of digestion with BseRI was not critical and it can be chosen anytime after 10 minutes from the addition of the restriction enzyme. For this and all subsequent experiments, an incubation time of 20 minutes from the addition of the restriction enzyme was chosen. FIG. 12 shows the standard curve of RNA polymerase DNA-binding activity. The points represent the 20 minute time points shown in FIG. 11. The binding activity was directly proportional to the amount of RNA polymerase added, in the range between 1 and 7 units of polymerase. A linear fitting of the data gave the following result:

$$y=10.5x+17.0$$

The standard curve can be used to quantitative the RNA polymerase binding activity of an unknown sample in the same way as described above for NFκB (Example 1).

C. Initiation of transcription and its inhibition

In order to measure the initiation of transcription RNA polymerase was added to 0.5 µg of pDNAB-tac plasmid following the same procedure described above for the measurement of DNA-binding activity. The 4 ribonucleotide triphosphates (ATP, CTP, GTP and UTP) were then added to the reaction mixture followed by BseRI and the amount of CCC DNA left was measured after 20 minutes using ethidium bromide fluorescence as in Example 1. In the presence of the 4 ribonucleotide triphosphates the RNA polymerase starts polymerizing an RNA molecule and it moves away from the promoter sequence, thereby de-protecting the BseRI cleavage site. Cleavage at this site can take place then.

FIG. 13 shows that addition of BseRI and the 4 ribonucleotide triphosphates results in cleavage of the plasmid by BseRI in 20 minutes of incubation in samples containing various amounts of RNA polymerase. The white bars represent the fluorescence units (i.e. the amount of protected plasmid) after addition of BseRI and before addition of the ribonucleotide triphosphates, while the hatched bars represent the fluorescent units remaining after 20 minutes after the addition of the 4 ribonucleotide triphosphates. The amount of protected plasmid after addition of the nucleotides tends to increase with the amount of RNA polymerase present. Without limiting the invention to any particular mechanism, this was probably due to a fraction of RNA polymerase that was active in binding to its cognate recognition sequence, but inactive in initiating transcription.

D. Inhibition of initiation of transcription

In order to measure the inhibition of the initiation of transcription, the effect of various concentrations of rifampicin on the de-protection of the BseRI site was measured. Rifampicin is an antibiotic used in the therapy of bacterial infections (e.g. tuberculosis) and it specifically targets bacterial RNA polymerase, by inhibiting its transcription activity. An amount of RNA polymerase that gave a protection of about 90% (0.24 U/sample of RNA polymerase from Pharmacia, Uppsala, Sweden) was added to 0.5 µg of plasmid pDNAB-tac under the same condition described supra. After 5 minutes of incubation, rifampicin and BseRI were added and the amount of uncleaved plasmid was measured after 20 minutes of incubation at 37° C. The 4 ribonucleotide triphosphates were then added and the amount of uncleaved plasmid was measured again after 20 more minutes of incubation at 37° C.

Figure 14:
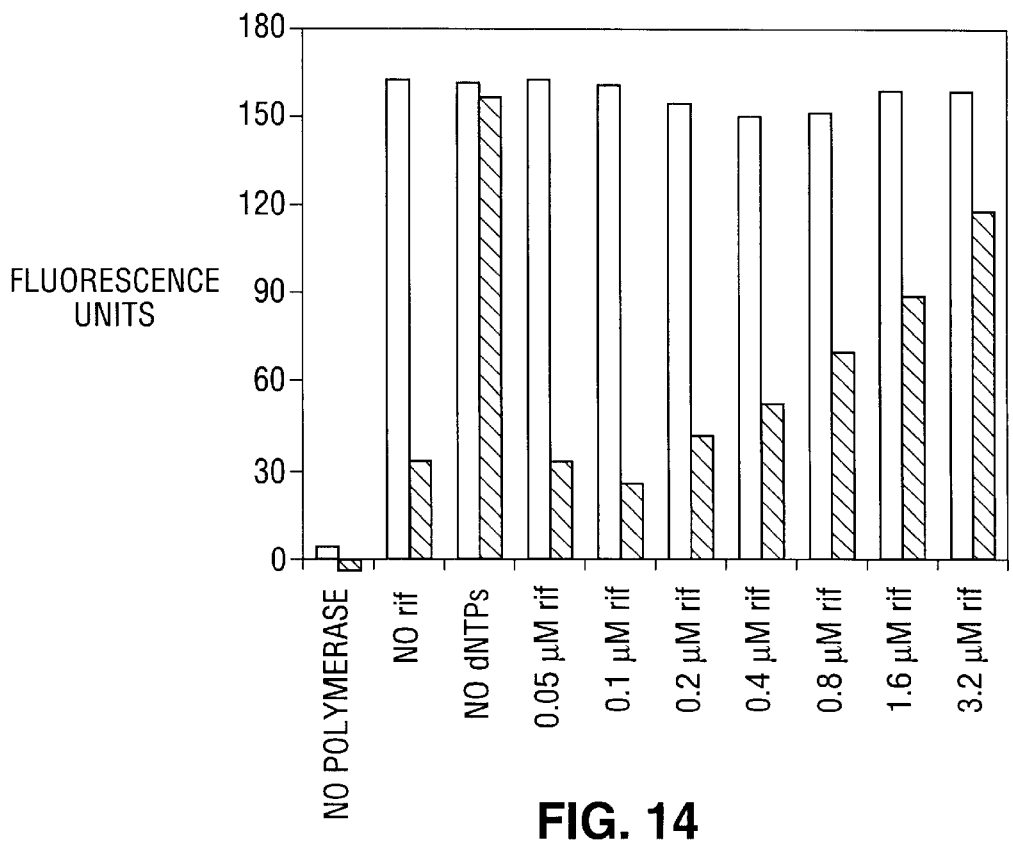
FIG. 14 is a bar graph showing the effects of the inhibitor rifampin on the binding activity and on the transcription initiation activity of *E. coli* RNA polymerase in the presence (shaded columns) and absence (open columns) of ribonucleotide triphosphates.

FIG. 14 shows the results of this experiment. The white bars represent the fluorescence units (i.e. the amount of uncleaved plasmid) before the addition of the 4 ribonucleoside triphosphates, while the hatched bars represent the fluorescence units left after addition of the 4 ribonucleotide triphosphates.

Importantly, rifampicin, showed a dose-dependent inhibition of the transcription initiation activity, but not of the binding of RNA polymerase to the promoter sequence. The relative effects of rifampicin on transcription was quantitated using the formula $$R = \frac{A - B}{A - C}$$

Where A is the amount of uncleaved plasmid in the negative control (without the four ribonucleotide triphosphates), B is the amount of uncleaved plasmid in the test samples, C is the amount of uncleaved plasmid in the positive control (with the four ribonucleotide triphosphates and without the inhibitor of initiation of transcription activity).

Figure 15:
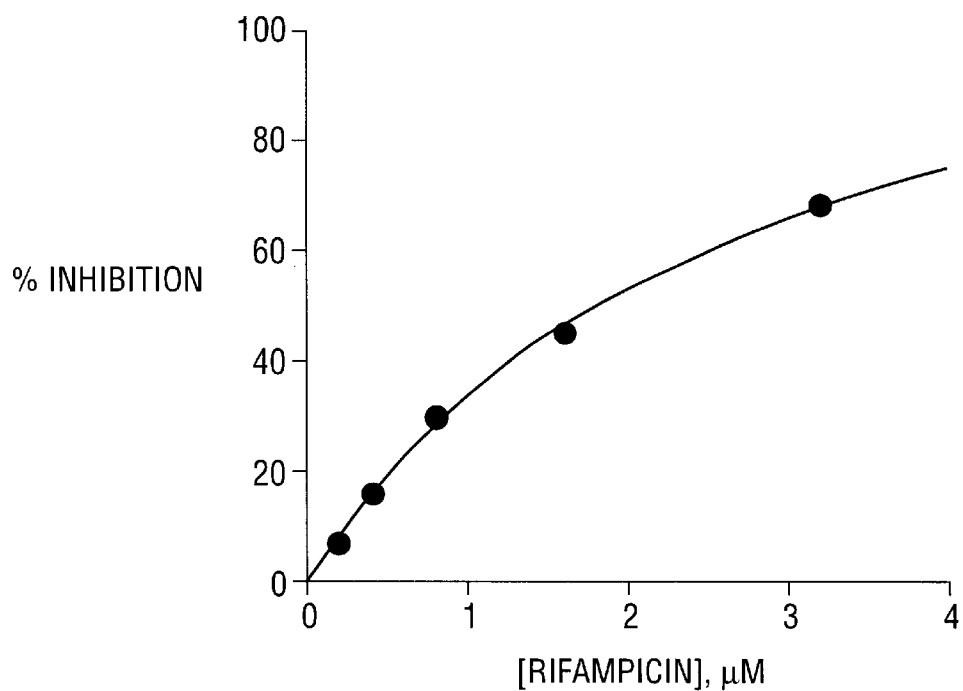
FIG. 15 is a graph showing the quantitation of the inhibitory activity of rifampicin on the transcription initiation by *E. coli* RNA polymerase.

The % inhibition of initiation of transcription activity was calculated as (1-R)* 100 and it was plotted in FIG. 15 for the range of concentrations of rifampicin from 0.2 µM to 3.2 µM. The points of FIG. 15 were fitted using a Michaelis-Menten equation that resulted in an apparent $K_i$ of rifampicin of 2.8 µM.

This example demonstrates the utility of the process in the discovery of new inhibitors of bacterial RNA polymerase and therefore potential new antibiotics.

It is clear from the above that the present invention provides compositions and methods for detecting and determining the DNA-binding activity of sequence-specific DNA-binding molecules with specificity and sensitivity. These compositions and methods offer the advantage over prior art methods of being rapid, quantitative, applicable to any sequence-specific DNA-binding molecule, and without the need to use radioactive isotopes. It is also clear from the above that the invention provides compositions and methods for detecting and determining the activity of RNA polymerases in initiating transcription with sensitivity and specificity. The methods of the invention are quantitative, and unlike the methods of prior art, the invention's methods are rapid, and do not require the use of radioactive isotopes.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly lintited to such specific embodiments. Indeed, various modifications of the described modes for carrying out the invention that are obvious to those skilled in the art and in fields related thereto are intended to be within the scope of the following claims.

What is claimed is:

1. A recombinant plasmid comprising: (a) a first region comprising a nucleotide sequence which specifically binds to a sequence-specific DNA-binding molecule; (b) a second region comprising a nucleotide sequence which binds to a restriction enzyme; and (c) a restriction site for said restriction enzyme; wherein said restriction site is located at a position selected from being within said first nucleotide sequence, within said second nucleotide sequence, substantially adjacent to said first nucleotide sequence, and substantially adjacent to said second nucleotide sequence.

2. The recombinant plasmid of claim 1, wherein said restriction site is comprised within said first nucleotide sequence, and said plasmid is selected from pDNAB-NFκB, pDNAB-TATA and pDNABtac.

3. The recombinant plasmid of claim 1, wherein said restriction site is comprised within said second nucleotide sequence, and said plasmid is pDNAB-or1.

4. The recombinant plasmid of claim 1, wherein said restriction site is substantially adjacent to said first nucleotide sequence, and said plasmid is pDNAB-or1.

5. The recombinant plasmid of claim 1, wherein said restriction site is substantially adjacent to said second nucleotide sequence, and said plasmid is selected from pDNAB-NFκB, pDNAB-TATA and pDNABtac.

6. The recombinant plasmid of claim 1, wherein said restriction enzyme is selected from AatII, AccI, AflI, AflIII, AhaII, AluI, AlwI, AlwNI, ApaI, ApaLI, AseI, Asp718, AvaI, AvaII, AvrII, BalI, BamHI, BanI, BanII, BbeI, BbvI, BbvII, BclI, BcnI, BglI, BglII, BseRIBsmI, BsmAI, Bsp1286I, BspHI, BspMI, BspMII, BsrI, BssHII, BstBI, BstEII, BstNI, BstUI, BstXI, BstYI, Bsu36I, Cfr10I, ClaI, DdeI, DpnI, DraI, DraIII, EaeI, EagI, EarI, Eco47III, EcoNI, EcoO109I, EcoRI, EcoRII, EcoRV, EspI, Fnu4HI, FokI, FspI, GdiII, HaeI, HaeII, HaeIII, HgaI, HgiAI, HihaI, HinCII, HinIII, HinfI, HinPI, HpaI, HpaII, HphI, KpnI, MaeI, MaeII, MaeIII, MboI, MboII, MluI, MnlI, MseI, MspI, NaeI, NarI, NciI, NcoI, NdeI, NheI, NlaIII, NlaIV, NotI, NruI, NsiI, Nsp7524I, NspBII, NspHI, PaeR7I, PflMI, PleI, PpuMI, PstI, PvuI, PvuII, RsaI, RsrII, SacI, SacII, SalI, Sau3AI, Sau96I, ScaI, ScrFI, SecI, SfaNI, SfiI, SmaI, SnaBI, SpeI, SphI, SplI, SspI, StuI, StyI, TaqI, Tth111I, Tth111II, XbaI, XcaI, XhoI, XmaI, XmnI.

7. The recombinant plasmid of claim 1, wherein said sequence-specific DNA-binding molecule is selected from nucleic acid sequence, amino acid sequence, derivative of nucleic acid sequence and derivative of amino acid sequence.

8. The recombinant plasmid of claim 7, wherein said sequence-specific DNA-binding molecule is a protein selected from λ cI repressor, TATA box binding protein, NFκB, bacterial mercury repressor, bacterial lac repressor, progesterone repressor, estrogen receptor, glucocorticoid receptor, androgen receptor, retinoid receptor family, thyroid receptor, p53, lac suppressor, AraC, DnaA, MerR, HSV-1 ICP4, UL9, c-Myc/c-Max, RecBCD, γ/δ resolvase, λ bacteriophage integrase complex, DNA photolyase, Ada protein, methylated Ada protein, Rag1/Rag2, bacterial RNA polymerase, c-Jun, AP2, SP1, TFIIB, vitamin D receptor, AP-1 complex, Sp1, CREB family, C/EBP family, Egr family, Ets family, Stat family, NF-1 family, YY1, Ap-2 factors, E2F family, IRF family, MEF-2, Myo-D/Myo-E, Oct family, Pit-1, USF-1/USF-2, c-Myb, Pbx-1, GATA family, NF-E2, serum response factor, T7 bacteriophage RNA polymerase, T3 bacteriophage RNA polymerase, SP6 bacteriophage RNA polymerase, eukaryotic RNA polymerase I, eukaryotic RNA polymerase II, eukaryotic RNA polymerase III, PBS1 phage RNA polymerase, PBS2 phage RNA polymerase, vaccinia virus RNA polymerase, *Escherichia coli* RNA polymerase, and mitochondrion RNA polymerase.

* * * * *

SEQUENCE LISTING

<160> NUMBER OF SEQ ID NOS: 72

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic

```
<400> SEQUENCE: 1
tatcaccgcc agaggta                                                    17

<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence:  Synthetic

<400> SEQUENCE: 2
ggtataaaag g                                                          11

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence:  Synthetic

<400> SEQUENCE: 3
ggtataaaag g                                                          11

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence:  Synthetic
<221> NAME/KEY: misc_feature
<222> LOCATION: (7)..(9)
<223> OTHER INFORMATION: The N at positions 7, 8, and 9 can be A, C, T,
      or G.

<400> SEQUENCE: 4
tgtacannnt gttct                                                      15

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence:  Synthetic

<400> SEQUENCE: 5
aggaaattcc                                                            10

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence:  Synthetic

<400> SEQUENCE: 6
tgtacaggat gttct                                                      15

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence:  Synthetic

<400> SEQUENCE: 7
atgtacagga tgttct                                                     16
```

```
<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (7)..(11)
<223> OTHER INFORMATION: The N at positions 7 through 11 can be A, C, T,
      or G.

<400> SEQUENCE: 8
ggttcannnn nagttcaagg tcagaggtca                                      30

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence: Synthetic

<400> SEQUENCE: 9
aggtcatgac ct                                                         12

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: Synthetic

<400> SEQUENCE: 10
tgttgacaat taatcctcct cgtataatgt gtgga                                35

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: Synthetic

<400> SEQUENCE: 11
agacaagcct                                                            10

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 12
aattgtgagc ggataacaat t                                               21

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 13
ccattcagag aagaaaccaa ttgtccatat                                      30

<210> SEQ ID NO 14
```

```
<211> LENGTH: 9
<212> TYPE: DNA
<213> ORGANISM: Artificial Sequence
<220> FEATURE:
<223> OTHER INFORMATION: Description of Artificial Sequence: Synthetic

<400> SEQUENCE: 14 ttatacaca                                                              9

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 15
gcttgactcc gtacatgagt acggaagtaa                                      30

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 16
atcacgcccc gatcgtccac acggagcgcg gctg                                 34

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 17
agcgttcgca cttcgtcc                                                   18

<210> SEQ ID NO 18
<211> LENGTH: 6
<212> TYPE: DNA
<213> ORGANISM: Artificial Sequence
<220> FEATURE:
<223> OTHER INFORMATION: Description of Artificial Sequence: Synthetic

<400> SEQUENCE: 18 cacgtc                                                                 6

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 19
taatacgact caatataggg aga                                             23

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence: Synthetic

<400> SEQUENCE: 20
```
tttaggtgac actata                                                16

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic

<400> SEQUENCE: 21
aattaaccct cactaaa                                               17

<210> SEQ ID NO 22
<211> LENGTH: 12
<212> TYPE: DNA
<213> ORGANISM: Artificial Sequence
<220> FEATURE:
<223> OTHER INFORMATION: Description of Artificial Sequence: Synthetic

<400> SEQUENCE: 22
gctggtggag ct                                                    12

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic

<400> SEQUENCE: 23
aaaaaagcat tgcttatcaa tttgttg                                    27

<210> SEQ ID NO 24
<211> LENGTH: 7
<212> TYPE: DNA
<213> ORGANISM: Artificial Sequence
<220> FEATURE:
<223> OTHER INFORMATION: Description of Artificial Sequence: Synthetic

<400> SEQUENCE: 24 aagcgca                                                          7

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (8)..(19)
<223> OTHER INFORMATION: The N at these positions can be A, C, T, or G.

<400> SEQUENCE: 25
cacagtgnnn nnnnnnnna caaaaacc                                    28

<210> SEQ ID NO 26
<211> LENGTH: 50
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (8)..(41)
<223> OTHER INFORMATION: The N at these positions can be A, C, T, or G.

<400> SEQUENCE: 26

```
cacagtgnnn nnnnnnnnnn nnnnnnnnnn nnnnnnnnnn nacaaaaacc          50
```

<210> SEQ ID NO 27
<211> LENGTH: 7
<212> TYPE: DNA
<213> ORGANISM: Artificial Sequence
<220> FEATURE:
<223> OTHER INFORMATION: Description of Artificial Sequence: Synthetic

<400> SEQUENCE: 27

```
tgagtca                                                          7
```

<210> SEQ ID NO 28
<211> LENGTH: 9
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (4)..(6)
<223> OTHER INFORMATION: The N at positions 4 through 6 can be A, C, T, or G.

<400> SEQUENCE: 28

```
gccnnnggc                                                        9
```

<210> SEQ ID NO 29
<211> LENGTH: 6
<212> TYPE: DNA
<213> ORGANISM: Artificial Sequence
<220> FEATURE:
<223> OTHER INFORMATION: Description of Artificial Sequence: Synthetic

<400> SEQUENCE: 29

```
gggcgg                                                           6
```

<210> SEQ ID NO 30
<211> LENGTH: 7
<212> TYPE: DNA
<213> ORGANISM: Artificial Sequence
<220> FEATURE:
<223> OTHER INFORMATION: Description of Artificial Sequence: Synthetic

<400> SEQUENCE: 30

```
tgactca                                                          7
```

<210> SEQ ID NO 31
<211> LENGTH: 10
<212> TYPE: DNA
<213> ORGANISM: Artificial Sequence
<220> FEATURE:
<223> OTHER INFORMATION: Description of Artificial Sequence: Synthetic

<400> SEQUENCE: 31

```
ggggcggggg                                                       10
```

<210> SEQ ID NO 32
<211> LENGTH: 8
<212> TYPE: DNA
<213> ORGANISM: Artificial Sequence
<220> FEATURE:
<223> OTHER INFORMATION: Description of Artificial Sequence: Synthetic

<400> SEQUENCE: 32

```
tgacctca                                                         8
```

<210> SEQ ID NO 33
<211> LENGTH: 8
<212> TYPE: DNA
<213> ORGANISM: Artificial Sequence
<220> FEATURE:
<223> OTHER INFORMATION: Description of Artificial Sequence: Synthetic

<400> SEQUENCE: 33 ttgcgcaa                                                              8

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 34
gcgggggcag cgggggcg                                                  18

<210> SEQ ID NO 35
<211> LENGTH: 8
<212> TYPE: DNA
<213> ORGANISM: Artificial Sequence
<220> FEATURE:
<223> OTHER INFORMATION: Description of Artificial Sequence: Synthetic

<400> SEQUENCE: 35 caggaagt                                                              8

<210> SEQ ID NO 36
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 36
attcctgtaa g                                                         11

<210> SEQ ID NO 37
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 37
ttctgggaat t                                                         11

<210> SEQ ID NO 38
<211> LENGTH: 12
<212> TYPE: DNA
<213> ORGANISM: Artificial Sequence
<220> FEATURE:
<223> OTHER INFORMATION: Description of Artificial Sequence: Synthetic

<400> SEQUENCE: 38
tttccccgaa at                                                        12

<210> SEQ ID NO 39
<211> LENGTH: 12
<212> TYPE: DNA
<213> ORGANISM: Artificial Sequence
<220> FEATURE:
<223> OTHER INFORMATION: Description of Artificial Sequence: Synthetic

<400> SEQUENCE: 39
tttctaggaa tt                                                               12

<210> SEQ ID NO 40
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 40
tttcccagaa a                                                                11

<210> SEQ ID NO 41
<211> LENGTH: 15
<212> TYPE: DNA
<213> ORGANISM: Artificial Sequence
<220> FEATURE:
<223> OTHER INFORMATION: Description of Artificial Sequence: Synthetic

<400> SEQUENCE: 41
tggattgaag ccaat                                                            15

<210> SEQ ID NO 42
<211> LENGTH: 9
<212> TYPE: DNA
<213> ORGANISM: Artificial Sequence
<220> FEATURE:
<223> OTHER INFORMATION: Description of Artificial Sequence: Synthetic

<400> SEQUENCE: 42 gcggccatc                                                                    9

<210> SEQ ID NO 43
<211> LENGTH: 8
<212> TYPE: DNA
<213> ORGANISM: Artificial Sequence
<220> FEATURE:
<223> OTHER INFORMATION: Description of Artificial Sequence: Synthetic

<400> SEQUENCE: 43 gcccgcgg                                                                     8

<210> SEQ ID NO 44
<211> LENGTH: 7
<212> TYPE: DNA
<213> ORGANISM: Artificial Sequence
<220> FEATURE:
<223> OTHER INFORMATION: Description of Artificial Sequence: Synthetic

<400> SEQUENCE: 44 ttcgcgc                                                                      7

<210> SEQ ID NO 45
<211> LENGTH: 12
<212> TYPE: DNA
<213> ORGANISM: Artificial Sequence
<220> FEATURE:
<223> OTHER INFORMATION: Description of Artificial Sequence: Synthetic

<400> SEQUENCE: 45
gaaaatgaaa tt                                                               12

<210> SEQ ID NO 46
<211> LENGTH: 10

```
<212> TYPE: DNA
<213> ORGANISM: Artificial Sequence
<220> FEATURE:
<223> OTHER INFORMATION: Description of Artificial Sequence: Synthetic

<400> SEQUENCE: 46
ctaaaaatag                                                              10

<210> SEQ ID NO 47
<211> LENGTH: 10
<212> TYPE: DNA
<213> ORGANISM: Artificial Sequence
<220> FEATURE:
<223> OTHER INFORMATION: Description of Artificial Sequence: Synthetic

<400> SEQUENCE: 47
ctatttttag                                                              10

<210> SEQ ID NO 48
<211> LENGTH: 6
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (3)..(4)
<223> OTHER INFORMATION: The N at these positions can be A, C, T, or G.

<400> SEQUENCE: 48 canntg                                                                   6

<210> SEQ ID NO 49
<211> LENGTH: 8
<212> TYPE: DNA
<213> ORGANISM: Artificial Sequence
<220> FEATURE:
<223> OTHER INFORMATION: Description of Artificial Sequence: Synthetic

<400> SEQUENCE: 49 atgcaaat                                                                 8

<210> SEQ ID NO 50
<211> LENGTH: 14
<212> TYPE: DNA
<213> ORGANISM: Artificial Sequence
<220> FEATURE:
<223> OTHER INFORMATION: Description of Artificial Sequence: Synthetic

<400> SEQUENCE: 50
ctgaatatga ataa                                                         14

<210> SEQ ID NO 51
<211> LENGTH: 6
<212> TYPE: DNA
<213> ORGANISM: Artificial Sequence
<220> FEATURE:
<223> OTHER INFORMATION: Description of Artificial Sequence: Synthetic

<400> SEQUENCE: 51 cacgtg                                                                   6

<210> SEQ ID NO 52
<211> LENGTH: 8
<212> TYPE: DNA
<213> ORGANISM: Artificial Sequence
<220> FEATURE:
<223> OTHER INFORMATION: Description of Artificial Sequence: Synthetic
```

```
<400> SEQUENCE: 52 taacggtt                                                                  8

<210> SEQ ID NO 53
<211> LENGTH: 8
<212> TYPE: DNA
<213> ORGANISM: Artificial Sequence
<220> FEATURE:
<223> OTHER INFORMATION: Description of Artificial Sequence: Synthetic

<400> SEQUENCE: 53 tgattgat                                                                  8

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (7)..(13)
<223> OTHER INFORMATION: The N at these positions can be A, C, T, or G.

<400> SEQUENCE: 54
tgataannnn nnntgataa                                                     19

<210> SEQ ID NO 55
<211> LENGTH: 10
<212> TYPE: DNA
<213> ORGANISM: Artificial Sequence
<220> FEATURE:
<223> OTHER INFORMATION: Description of Artificial Sequence: Synthetic

<400> SEQUENCE: 55
tgctgagtca                                                               10

<210> SEQ ID NO 56
<211> LENGTH: 10
<212> TYPE: DNA
<213> ORGANISM: Artificial Sequence
<220> FEATURE:
<223> OTHER INFORMATION: Description of Artificial Sequence: Synthetic

<400> SEQUENCE: 56
ccatattagg                                                               10

<210> SEQ ID NO 57
<211> LENGTH: 11
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (4)..(8)
<223> OTHER INFORMATION: The N at these positions can be A, C, T, or G.

<400> SEQUENCE: 57 gccnnnnnggc                                                              11

<210> SEQ ID NO 58
<211> LENGTH: 12
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
```

```
<222> LOCATION: (4)..(9)
<223> OTHER INFORMATION: The N at these positions can be A, C, T, or G.

<400> SEQUENCE: 58
ccannnnnnt gg                                                              12

<210> SEQ ID NO 59
<211> LENGTH: 11
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (4)..(8)
<223> OTHER INFORMATION: The N at these positions can be A, C, T, or G.

<400> SEQUENCE: 59
cctnnnnnag g                                                               11

<210> SEQ ID NO 60
<211> LENGTH: 11
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (4)..(8)
<223> OTHER INFORMATION: The N at these positions can be A, C, T, or G.

<400> SEQUENCE: 60
ccannnnntg g                                                               11

<210> SEQ ID NO 61
<211> LENGTH: 13
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (5)..(9)
<223> OTHER INFORMATION: The N at these positions can be A, C, T, or G.

<400> SEQUENCE: 61
ggccnnnnng gcc                                                             13

<210> SEQ ID NO 62
<211> LENGTH: 10
<212> TYPE: DNA
<213> ORGANISM: Artificial Sequence
<220> FEATURE:
<223> OTHER INFORMATION: Description of Artificial Sequence: Synthetic
<221> NAME/KEY: misc_feature
<222> LOCATION: (4)..(7)
<223> OTHER INFORMATION: The N at these positions can be A, C, T, or G.

<400> SEQUENCE: 62 gaannnnttc                                                                 10

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 63
gatcgaggag ggaaattcct gca                                                  23
```

<210> SEQ ID NO 64
<211> LENGTH: 28
<212> TYPE: DNA
<213> ORGANISM: Artificial Sequence
<220> FEATURE:
<223> OTHER INFORMATION: Description of Artificial Sequence: Synthetic

<400> SEQUENCE: 64
gatcgaggag gggtataaaa ggcctgca                                      28

<210> SEQ ID NO 65
<211> LENGTH: 17
<212> TYPE: DNA
<213> ORGANISM: Artificial Sequence
<220> FEATURE:
<223> OTHER INFORMATION: Description of Artificial Sequence: Synthetic

<400> SEQUENCE: 65
tatcaccgcc agaggta                                                 17

<210> SEQ ID NO 66
<211> LENGTH: 56
<212> TYPE: DNA
<213> ORGANISM: Artificial Sequence
<220> FEATURE:
<223> OTHER INFORMATION: Description of Artificial Sequence: Synthetic

<400> SEQUENCE: 66
gatcgaggag atatcaccgc cagaggtaaa atagttatca ccgccagagg tatgca       56

<210> SEQ ID NO 67
<211> LENGTH: 46
<212> TYPE: DNA
<213> ORGANISM: Artificial Sequence
<220> FEATURE:
<223> OTHER INFORMATION: Description of Artificial Sequence: Synthetic

<400> SEQUENCE: 67
agcttgttga caattaatcc tcctcctcgt ataatgtgtg gatgac                  46

<210> SEQ ID NO 68
<211> LENGTH: 15
<212> TYPE: DNA
<213> ORGANISM: Artificial Sequence
<220> FEATURE:
<223> OTHER INFORMATION: Description of Artificial Sequence: Synthetic

<400> SEQUENCE: 68
ggaatttccc tcctc                                                   15

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 69
ggccttttat acccctcctc                                              20

<210> SEQ ID NO 70
<211> LENGTH: 48
<212> TYPE: DNA
<213> ORGANISM: Artificial Sequence
<220> FEATURE:
<223> OTHER INFORMATION: Description of Artificial Sequence: Synthetic -continued

```
<400> SEQUENCE: 70
tacctctggc ggtgataact attttacctc tggcggtgat atctcctc                    48

<210> SEQ ID NO 71
<211> LENGTH: 38
<212> TYPE: DNA
<213> ORGANISM: Artificial Sequence
<220> FEATURE:
<223> OTHER INFORMATION: Description of Artificial Sequence:  Synthetic

<400> SEQUENCE: 71
tccacacatt atacgaggag gaggattaat tgtcaaca                               38

<210> SEQ ID NO 72
<211> LENGTH: 46
<212> TYPE: DNA
<213> ORGANISM: Artificial Sequence
<220> FEATURE:
<223> OTHER INFORMATION: Description of Artificial Sequence:  Synthetic

<400> SEQUENCE: 72
agcttgttga caattaatcc tcctcctcgt ataatgtgtg gatgac                      46
```